US012680104B2

(12) United States Patent
Brennan et al.

(10) Patent No.: US 12,680,104 B2
(45) Date of Patent: Jul. 14, 2026

(54) DNA APTAMERS FOR EOSINOPHIL PEROXIDASE DETECTION

(71) Applicant: McMaster University, Hamilton (CA)

(72) Inventors: John D. Brennan, Dundas (CA); Monsur Ali, Hamilton (CA); Michael Wolfe, Hamilton (CA); Dawn White, Bolton (CA); Manali Mukherjee, Hamilton (CA); Parameswaran Nair, Dundas (CA); Alfredo Capretta, Dundas (CA)

(73) Assignee: MCMASTER UNIVERSITY, Hamilton (CA)

( * ) Notice: Subject to any disclaimer, the term of this patent is extended or adjusted under 35 U.S.C. 154(b) by 785 days.

(21) Appl. No.: 17/966,575

(22) Filed: Oct. 14, 2022

(65) Prior Publication Data

US 2023/0295635 A1      Sep. 21, 2023

Related U.S. Application Data

(60) Provisional application No. 63/256,138, filed on Oct. 15, 2021.

(30) Foreign Application Priority Data

Oct. 15, 2021    (CA) ................................. CA 3134378

(51) Int. Cl.
C12N 15/115      (2010.01)
C12Q 1/28      (2006.01)

(52) U.S. Cl.
CPC .............. C12N 15/115 (2013.01); C12Q 1/28 (2013.01); *C12N 2310/16* (2013.01)

(58) Field of Classification Search
CPC .......................... C12N 15/115; C12N 2310/16
See application file for complete search history.

(56) References Cited

PUBLICATIONS

Bruno. In Vitro Selection of DNA to Chloroaromatics Using Magnetic Microbead-Based Affinity Separation and Fluorescence Detection. Biochemical and Biophysical Research Communications, vol. 234(1), published May 8, 1997, pp. 117-120.

Duan et al. Selection and characterization of aptamers against *Salmonella typhimurium* using whole-bacterium Systemic Evolution of Ligands by Exponential Enrichment (SELEX). Journal of Agricultural and Food Chemistry, vol. 61(13), published Mar. 11, 2013, pp. 3229-3234.
Ali et al. Fluorogenic DNAzyme Probes as Bacterial Indicators. Angewandte Chemie International Edition, vol. 50(16), first published Mar. 15, 2011, pp. 3751-3754.
Altschul et al. Gapped Blast and PSI-Blast: a new generation of protein database search programs. Nucleic Acids Research, vol. 25(17), published Sep. 1, 1997, pp. 3389-3402.
Ochkur et al. A sensitive high throughput ELISA for human eosinophil peroxidase: A specific assay to quantify eosinophil degranulation from patient-derived sources. Journal of Immunological Methods, vol. 384 (1-2), published online Jun. 28, 2012, pp. 10-20.
Wolfe et al. Rapid quantification of sputum eosinophil peroxidase on a lateral flow test strip. Letter to the Editor. Allergy, vol. 74 (1), first published Dec. 28, 2018, pp. 1176-1178.
Nair et al. Eosinophil peroxidase in sputum represents a unique biomarker of airway eosinophilia. Allergy, vol. 68(9), published online Aug. 9, 2013, pp. 1177-1184.
You et al. A fast and ultrasensitive ELISA based on rolling circle amplification. Analyst, vol. 146 (9), published Apr. 6, 2021, pp. 2871-2877.
Pizzichini et al. Measurements of inflammatory indices in induced sputum: effects of selection of sputum to minimize salivary contamination. European Respiratory Journal, vol. 9, published Jun. 1, 1996, pp. 1174-1180.
Kjarsgaard et al. Underestimation of airway luminal eosinophilia by quantitative sputum cytometry. Allergy, Asthma & Clinical Immunology, vol. 17(1):63, published Jul. 5, 2021, 7 pages.
Belda et al. Induced Sputum Cell Counts in Healthy Adults. American Journal of Respiratory and Critical Care Medicine, vol. 161, published Feb. 2000, pp. 475-478.
Sajid et al. Design, Formats and Applications of Lateral Flow Assay: A literature review. Journal of Saudi Chemical Society, vol. 19, published online Sep. 16, 2014, pp. 689-705.
Bahadir and Sezgintürk. Lateral flow assays: Principles, designs and labels. Trends in Analytical Chemistry, vol. 82, published Sep. 2016, pp. 286-306.

*Primary Examiner* — J. E. Angell

(74) *Attorney, Agent, or Firm* — SMART & BIGGAR LP

(57) ABSTRACT

This disclosure relates to DNA aptamers that bind eosinophil peroxidase, including uses thereof, such as in eosinophil peroxidase detection assays. Also provided is a method for detecting the presence of eosinophil peroxidase in a sample, using the DNA aptamers that bind eosinophil peroxidase. Further provided is a kit for detecting the presence of eosinophil peroxidase in a sample, using the DNA aptamers that bind eosinophil peroxidase.

17 Claims, 19 Drawing Sheets

Specification includes a Sequence Listing.

FIG. 1C

| Name | Random domain | | | | Enrichment |
|---|---|---|---|---|---|
| EAP1-01: | CACGGGGATC | GGGTGGGGGC | TAGGCGGCGT | GTGCACGGGG | 7.4% |
| EAP1-05: | CAGGGGGACA | GTGCAAAGGG | GTAGGGAGGG | GGCTAGGGGG | 0.45% |
| EAP1-08: | CAGTTGCCGG | TGGGGTGACC | CGGTGGGGGA | GGGTGTGGGG | 0.32% |
| EAP1-15: | CGGGGGAGCA | AGGTGTAGGG | GTAGGGGGCC | ATGCGAGGGG | 0.24% |
| EAP1-20: | AGCAGCGGGC | GGGGGCCAGT | GGGGGATGTA | GCCGGGGGTG | 0.17% |
| EAP2-01: | CGCGGGAGGA | GACTGGTGTA | GGGGGCATGG | GATGGCCTGG | 4.29% |
| EAP2-09: | ACGACCGGTG | TAGAGGGGGG | TATACGGAAT | GGGGGTTGTG | 0.61% |
| EAP2-10: | AGGGAGGGGG | CGGTTAGGGA | ATGGTGGTCC | GGGCGGGGTA | 0.55% |
| EAP2-18: | ATGGGGATAT | CCGGCGGGGG | CATCAGGGGG | GAGTGCGGGT | 0.35% |
| EAP2-40: | CAGGGGGCGC | GGGAGGGGGC | CTGACGTCGA | GGGGGTTGGG | 0.19% |

FIG. 1D

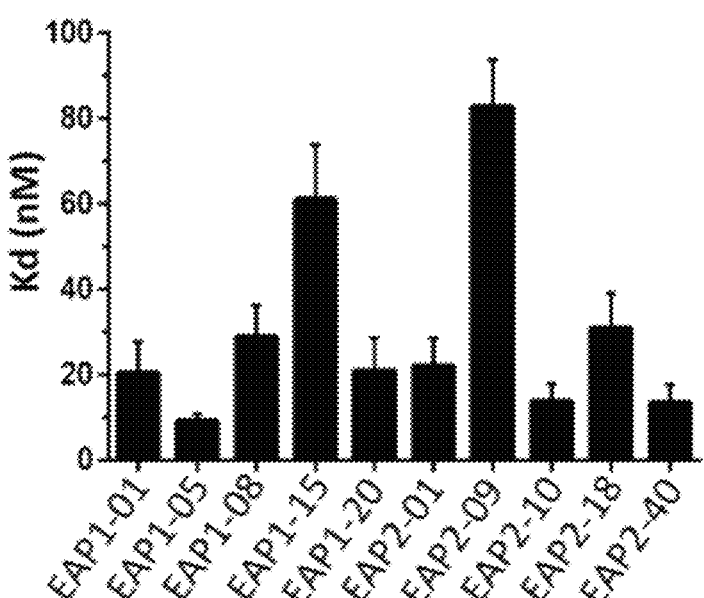

FIG. 1E

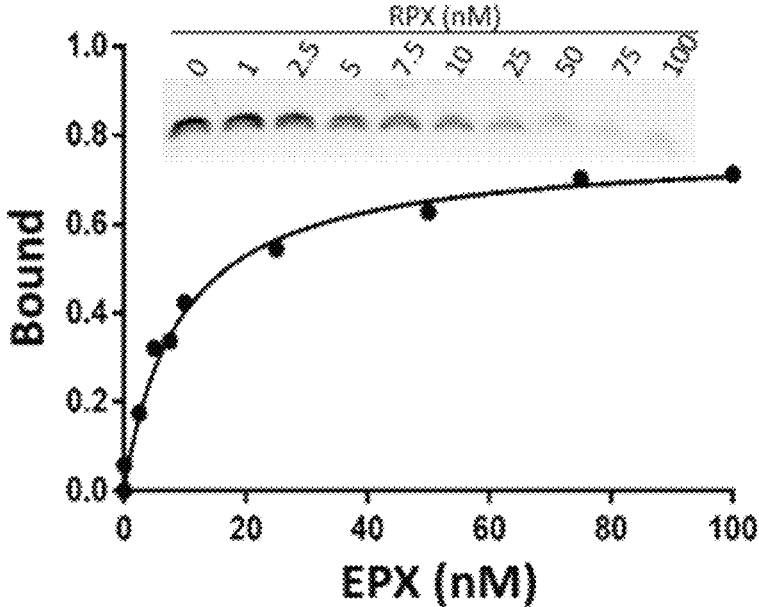

FIG. 2A

```
EAP1-05:
ATGCCATCCTA CCAACCAGGGG GACAGTGCAAA GGGGTAGGGAG
GGGGCTAGGGG GGAGCTCTGAA CTCG
EAP1-05T1:
~~~~~~~~~~~ ~~~~~~CAGG GGGACAGTGC AAAGGGGTAG GGAGGGGGCT
AGGGGG~~~~~ ~~~~~~~~~~
EAP1-05T2:
~~~CCATCCT ACCAACCAGG GGGACAGTGC AAAGGGGTAG GGAG~~~~~~
~~~~~~~~~~ ~~~~~~~~~~
EAP1-05T3:
ATGCCATCCT ACCAACCAGG GGGACAGTGC AAAGGG~~~~ ~~~~~~~~~~
~~~~~~~AGC TCTGAACTCG
EAP1-05T4:
ATGCCATCCT ACCAACCAGA AAGACAGTGC AAAGAAATAG AAAGAGAGCT
AGAAGAAAGC TCTGAACTCG
```

FIG. 2B (SEQ ID NO: 38)

(SEQ ID NO: 30)

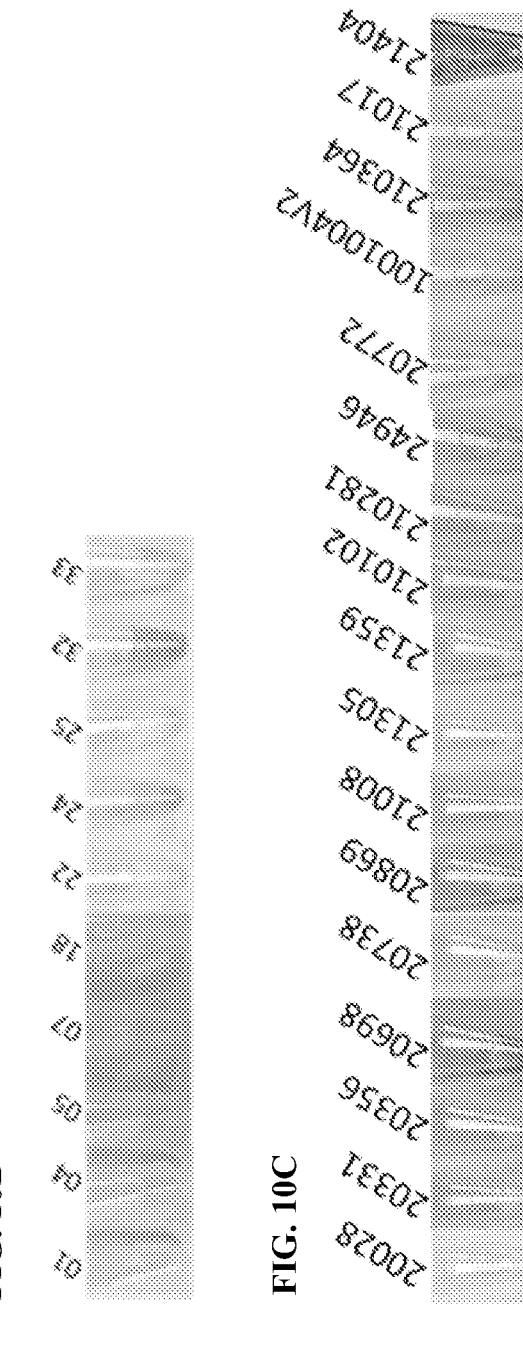
FIG. 10B
FIG. 10C
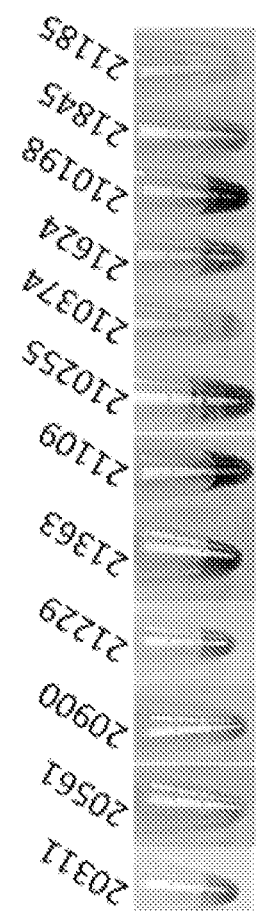
FIG. 10E
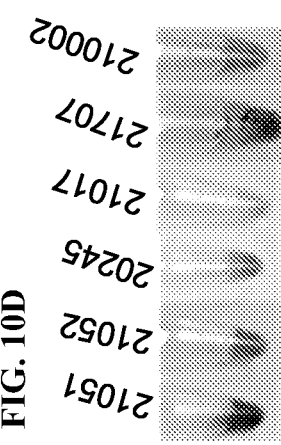
FIG. 10D

Dotted line: experimental lower cut-off 0.32

SEQUENCE LISTING

```
Sequence total quantity: 38
SEQ ID NO: 1          moltype = DNA  length = 70
FEATURE               Location/Qualifiers
misc_difference       17..56
                      note = n is a, c, g, or t
source                1..70
                      mol_type = other DNA
                      organism = synthetic construct
SEQUENCE: 1
atgccatcct accaacnnnn nnnnnnnnnn nnnnnnnnnn nnnnnnnnnn nnnnnngagc   60
tctgaactgg                                                          70

SEQ ID NO: 2          moltype = DNA  length = 16
FEATURE               Location/Qualifiers
misc_feature          1..16
                      note = Synthetic construct
source                1..16
                      mol_type = other DNA
                      organism = synthetic construct
SEQUENCE: 2
atgccatcct accaac                                                   16

SEQ ID NO: 3          moltype = DNA  length = 16
FEATURE               Location/Qualifiers
source                1..16
                      mol_type = other DNA
                      organism = synthetic construct
modified_base         1
                      mod_base = OTHER
                      note = Fluorescein deoxyadenosine
SEQUENCE: 3
atgccatcct accaac                                                   16

SEQ ID NO: 4          moltype = DNA  length = 14
FEATURE               Location/Qualifiers
```

-continued

```
misc_feature          1..14
                      note = Synthetic construct
source                1..14
                      mol_type = other DNA
                      organism = synthetic construct
SEQUENCE: 4
ccagttcaga gctc                                                  14

SEQ ID NO: 5          moltype = DNA  length = 14
FEATURE               Location/Qualifiers
misc_feature          1..14
                      note = Synthetic construct
source                1..14
                      mol_type = other DNA
                      organism = synthetic construct
SEQUENCE: 5
gagctctgaa ctgg                                                  14

SEQ ID NO: 6          moltype = DNA  length = 20
FEATURE               Location/Qualifiers
misc_feature          20
                      note = The 3' of the deoxyadenosine is attached
                       through the triethylene glycol spacer to SEQ ID NO: 37
source                1..20
                      mol_type = other DNA
                      organism = synthetic construct
SEQUENCE: 6
aaaaaaaaaa aaaaaaaaaa                                            20

SEQ ID NO: 7          moltype = DNA  length = 27
FEATURE               Location/Qualifiers
source                1..27
                      mol_type = other DNA
                      organism = synthetic construct
misc_feature          1..27
                      note = Synthetic construct
SEQUENCE: 7
gcggcccatt cttcatttta gggccgc                                    27

SEQ ID NO: 8          moltype = DNA  length = 70
FEATURE               Location/Qualifiers
misc_feature          1..70
                      note = Synthetic construct
source                1..70
                      mol_type = other DNA
                      organism = synthetic construct
SEQUENCE: 8
atgccatcct accaaccacg gggatcgggt gggggctagg cggcgtgtgc acgggggagc  60
tctgaactgg                                                       70

SEQ ID NO: 9          moltype = DNA  length = 70
FEATURE               Location/Qualifiers
misc_feature          1..70
                      note = Synthetic construct
source                1..70
                      mol_type = other DNA
                      organism = synthetic construct
SEQUENCE: 9
atgccatcct accaaccagg gggacagtgc aaaggggtag ggaggggget aggggggagc  60
tctgaactgg                                                       70

SEQ ID NO: 10         moltype = DNA  length = 70
FEATURE               Location/Qualifiers
misc_feature          1..70
                      note = Synthetic construct
source                1..70
                      mol_type = other DNA
                      organism = synthetic construct
SEQUENCE: 10
atgccatcct accaaccagt tgccggtggg gtgacccggt ggggggaggt gtggggggagc  60
tctgaactgg                                                       70

SEQ ID NO: 11         moltype = DNA  length = 70
FEATURE               Location/Qualifiers
misc_feature          1..70
                      note = Synthetic construct
source                1..70
                      mol_type = other DNA
                      organism = synthetic construct
```

-continued

```
SEQUENCE: 11
atgccatcct accaaccggg ggagcaaggt gtaggggtag ggggccatgc gagggggagc    60
tctgaactgg                                                           70

SEQ ID NO: 12              moltype = DNA   length = 70
FEATURE                    Location/Qualifiers
misc_feature               1..70
                           note = Synthetic construct
source                     1..70
                           mol_type = other DNA
                           organism = synthetic construct
SEQUENCE: 12
atgccatcct accaacagca gcgggcgggg gccagtgggg gatgtagccg ggggtggagc    60
tctgaactgg                                                           70

SEQ ID NO: 13              moltype = DNA   length = 70
FEATURE                    Location/Qualifiers
misc_feature               1..70
                           note = Synthetic construct
source                     1..70
                           mol_type = other DNA
                           organism = synthetic construct
SEQUENCE: 13
atgccatcct accaaccgcg ggaggagact ggtgtagggg gcatgggatg gcctgggagc    60
tctgaactgg                                                           70

SEQ ID NO: 14              moltype = DNA   length = 70
FEATURE                    Location/Qualifiers
misc_feature               1..70
                           note = Synthetic construct
source                     1..70
                           mol_type = other DNA
                           organism = synthetic construct
SEQUENCE: 14
atgccatcct accaacacga ccggtgtaga ggggggtata cggaatgggg gttgtggagc    60
tctgaactgg                                                           70

SEQ ID NO: 15              moltype = DNA   length = 70
FEATURE                    Location/Qualifiers
misc_feature               1..70
                           note = Synthetic construct
source                     1..70
                           mol_type = other DNA
                           organism = synthetic construct
SEQUENCE: 15
atgccatcct accaacaggg aggggcggt tagggaatgg tggtccgggc ggggtagagc     60
tctgaactgg                                                           70

SEQ ID NO: 16              moltype = DNA   length = 70
FEATURE                    Location/Qualifiers
misc_feature               1..70
                           note = Synthetic contruct
source                     1..70
                           mol_type = other DNA
                           organism = synthetic construct
SEQUENCE: 16
atgccatcct accaacatgg ggatatccgg cgggggcatc aggggggagt gcgggtgagc    60
tctgaactgg                                                           70

SEQ ID NO: 17              moltype = DNA   length = 70
FEATURE                    Location/Qualifiers
misc_feature               1..70
                           note = Synthetic construct
source                     1..70
                           mol_type = other DNA
                           organism = synthetic construct
SEQUENCE: 17
atgccatcct accaaccagg gggcgcggga ggggccctga cgtcgagggg gttggggagc    60
tctgaactgg                                                           70

SEQ ID NO: 18              moltype = DNA   length = 40
FEATURE                    Location/Qualifiers
misc_feature               1..40
                           note = Synthetic construct
source                     1..40
                           mol_type = other DNA
                           organism = synthetic construct
SEQUENCE: 18
cacggggatc gggtgggggc taggcggcgt gtgcacgggg                          40
```

```
SEQ ID NO: 19           moltype = DNA   length = 40
FEATURE                 Location/Qualifiers
misc_feature            1..40
                        note = Synthetic
source                  1..40
                        mol_type = other DNA
                        organism = synthetic construct
SEQUENCE: 19
caggggaca gtgcaaaggg gtagggaggg ggctagggg                         40

SEQ ID NO: 20           moltype = DNA   length = 40
FEATURE                 Location/Qualifiers
misc_feature            1..40
                        note = Synthetic construct
source                  1..40
                        mol_type = other DNA
                        organism = synthetic construct
SEQUENCE: 20
cagttgccgg tggggtgacc cggtggggga gggtgtgggg                       40

SEQ ID NO: 21           moltype = DNA   length = 40
FEATURE                 Location/Qualifiers
misc_feature            1..40
                        note = Synthetic construct
source                  1..40
                        mol_type = other DNA
                        organism = synthetic construct
SEQUENCE: 21
cggggggagca aggtgtaggg gtagggggcc atgcgagggg                      40

SEQ ID NO: 22           moltype = DNA   length = 40
FEATURE                 Location/Qualifiers
misc_feature            1..40
                        note = Synthetic construct
source                  1..40
                        mol_type = other DNA
                        organism = synthetic construct
SEQUENCE: 22
agcagcgggc gggggccagt gggggatgta gccggggggtg                      40

SEQ ID NO: 23           moltype = DNA   length = 40
FEATURE                 Location/Qualifiers
misc_feature            1..40
                        note = Synthetic construct
source                  1..40
                        mol_type = other DNA
                        organism = synthetic construct
SEQUENCE: 23
cgcgggagga gactggtgta gggggcatgg gatggcctgg                       40

SEQ ID NO: 24           moltype = DNA   length = 40
FEATURE                 Location/Qualifiers
misc_feature            1..40
                        note = Synthetic construct
source                  1..40
                        mol_type = other DNA
                        organism = synthetic construct
SEQUENCE: 24
acgaccggtg tagagggggg tatacggaat gggggttgtg                       40

SEQ ID NO: 25           moltype = DNA   length = 40
FEATURE                 Location/Qualifiers
misc_feature            1..40
                        note = Synthetic construct
source                  1..40
                        mol_type = other DNA
                        organism = synthetic construct
SEQUENCE: 25
agggaggggg cggttaggga atggtggtcc gggcgggggta                      40

SEQ ID NO: 26           moltype = DNA   length = 40
FEATURE                 Location/Qualifiers
misc_feature            1..40
                        note = Synthetic construct
source                  1..40
                        mol_type = other DNA
                        organism = synthetic construct
SEQUENCE: 26
```

-continued

```
atggggatat ccggcggggg catcagggggg gagtgcgggt                           40

SEQ ID NO: 27          moltype = DNA   length = 40
FEATURE                Location/Qualifiers
misc_feature           1..40
                       note = Synthetic construct
source                 1..40
                       mol_type = other DNA
                       organism = synthetic construct
SEQUENCE: 27
caggggggcgc gggaggggggc ctgacgtcga gggggttggg                          40

SEQ ID NO: 28          moltype = DNA   length = 41
FEATURE                Location/Qualifiers
misc_feature           1..41
                       note = Synthetic construct
source                 1..41
                       mol_type = other DNA
                       organism = synthetic construct
SEQUENCE: 28
ccatcctacc aaccaggggg acagtgcaaa ggggtaggga g                          41

SEQ ID NO: 29          moltype = DNA   length = 48
FEATURE                Location/Qualifiers
misc_feature           1..48
                       note = Synthetic construct
source                 1..48
                       mol_type = other DNA
                       organism = synthetic construct
SEQUENCE: 29
atgccatcct accaataggg aggggggctag ggggggagctc tgaactcg                 48

SEQ ID NO: 30          moltype = DNA   length = 49
FEATURE                Location/Qualifiers
misc_feature           1..49
                       note = Synthetic construct
source                 1..49
                       mol_type = other DNA
                       organism = synthetic construct
SEQUENCE: 30
atgccatcct accaaccagg gggacagtgc aaagggagct ctgaactcg                  49

SEQ ID NO: 31          moltype = DNA   length = 70
FEATURE                Location/Qualifiers
misc_feature           1..70
                       note = Synthetic construct
source                 1..70
                       mol_type = other DNA
                       organism = synthetic construct
SEQUENCE: 31
atgccatcct accaaccaga aagacagtgc aaagaaatag aaagagagct agaagaaagc      60
tctgaactcg                                                            70

SEQ ID NO: 32          moltype = DNA   length = 41
FEATURE                Location/Qualifiers
source                 1..41
                       mol_type = other DNA
                       organism = synthetic construct
modified_base          1
                       mod_base = OTHER
                       note = fluorescein deoxycytidine
SEQUENCE: 32
ccatcctacc aaccaggggg acagtgcaaa ggggtaggga g                          41

SEQ ID NO: 33          moltype = DNA   length = 48
FEATURE                Location/Qualifiers
source                 1..48
                       mol_type = other DNA
                       organism = synthetic construct
modified_base          1
                       mod_base = OTHER
                       note = fluorescein deoxyadenosine
SEQUENCE: 33
atgccatcct accaataggg aggggggctag ggggggagctc tgaactcg                 48

SEQ ID NO: 34          moltype = DNA   length = 49
FEATURE                Location/Qualifiers
modified_base          1
                       mod_base = OTHER
```

-continued

```
                         note = fluorescein deoxyadenosine
source                   1..49
                         mol_type = other DNA
                         organism = synthetic construct
SEQUENCE: 34
atgccatcct accaaccagg gggacagtgc aaagggagct ctgaactcg            49

SEQ ID NO: 35           moltype = DNA   length = 70
FEATURE                 Location/Qualifiers
misc_feature            1..70
                         note = Synthetic construct
source                   1..70
                         mol_type = other DNA
                         organism = synthetic construct
modified_base           1
                         mod_base = OTHER
                         note = fluorescein deoxyadenosine
SEQUENCE: 35
atgccatcct accaaccaga aagacagtgc aaagaaatag aaagagagct agaagaaagc  60
tctgaactcg                                                        70

SEQ ID NO: 36           moltype = DNA   length = 59
FEATURE                 Location/Qualifiers
source                   1..59
                         mol_type = other DNA
                         organism = synthetic construct
modified_base           1
                         mod_base = OTHER
                         note = Biotinylated thymidine
SEQUENCE: 36
tttttttttt atgccatcct accaaccagg gggacagtgc aaagggagct ctgaactcg   59

SEQ ID NO: 37           moltype = DNA   length = 14
FEATURE                 Location/Qualifiers
source                   1..14
                         mol_type = other DNA
                         organism = synthetic construct
misc_feature            1
                         note = The 5' of the deoxycytidine is attached through
                          the triethylene glycol spacer to SEQ ID NO: 6
SEQUENCE: 37
ccagttcaga gctc                                                   14

SEQ ID NO: 38           moltype = DNA   length = 70
FEATURE                 Location/Qualifiers
source                   1..70
                         mol_type = other DNA
                         organism = synthetic construct
SEQUENCE: 38
atgccatcct accaaccagg gggacagtgc aaagggggtag ggaggggggct aggggggagc  60
tctgaactcg                                                        70
```

1

DNA APTAMERS FOR EOSINOPHIL PEROXIDASE DETECTION

RELATED APPLICATION

This disclosure claims priority and benefit of U.S. Provisional Patent Application Ser. No. 63/256,138 filed Oct. 15, 2021, and Canadian Patent Application No. 3,134,378 filed Oct. 15, 2021, incorporated herein by reference in their entireties.

INCORPORATION OF SEQUENCE LISTING

A computer readable form of the Sequence Listing "93689043_SequenceListing.xml" (51,333 bytes), submitted via Patent Center and created on Feb. 1, 2026, is herein incorporated by reference.

FIELD

The present disclosure relates to DNA aptamers, and in particular, to DNA aptamers for binding eosinophil peroxidase, including uses thereof, such as in a method or kit for detecting eosinophil peroxidase detection.

BACKGROUND

With a worldwide prevalence in over 300 million people, asthma remains as one of the most widespread chronic diseases on the planet. In Canada, this translates into a ~\$2.1 billion dollar healthcare burden per annum. One limitation to current clinical asthma management is correctly and rapidly identifying the underlying causes of bronchial inflammation, and personalizing treatment based on those findings. The current gold standard for doing that involves sputum induction followed by histological staining, and has been proven to be extremely effective in managing asthma. However, this technique is limited in application owing to accessibility to a laboratory, and the need for equipment and trained technicians to perform the testing. A simpler alternative is to perform high-throughput assays such as an enzyme-linked immunosorbent assay (ELISA) on the fluid-fraction of the processed sputa, using surrogate markers for eosinophils, a leucocyte that is highly linked to prevalence and severity in asthma. Unfortunately, this is also limited by the need for lengthy processing times, multiple assay steps to separate cellular and fluid fractions, and the need for expensive instrumentation. Hence, there remains a major need for simple biosensing platforms to rapidly identify and quantify the presence of eosinophils in sputum samples.

Eosinophils are granulocytes that play a significant role in the pathogenesis of asthma and other airway diseases. The use of eosinophil peroxidase (EPX) has been validated as an ideal biomarker to identify the presence of eosinophils when compared to other surrogate markers. While antibodies have already been developed for this target, recent research has shown that the possibility of an autoimmune response to eosinophil degranulation products such as EPX can result in a high polyclonal IgG presence in the airways. This high IgG presence can complicate rapid antibody lateral flow and ELISA detection systems, requiring additional sample processing steps.

The background herein is included solely to explain the context of the disclosure. This is not to be taken as an admission that any of the material referred to was published, known, or part of the common general knowledge as of the priority date.

2

SUMMARY

The present disclosure describes the selection and improvement of a new DNA aptamer for EPX, and its use for the development of a colorimetric pull-down assay to detect EPX in patient sputum samples. A rapid sputum processing method that reduces both the time and technical complexity of sample preparation, resulting in a simplified assay that can be performed in under 1 hour, is also disclosed. The validation of the pull-down assay using clinical samples from both eosinophilia positive and negative patients, as determined by eosinophil cell counts and ELISA assays, described herein demonstrates no interferences from autoantibodies using the disclosed method or kit.

In accordance with an aspect, there is provided a DNA aptamer that binds eosinophil peroxidase, wherein the aptamer comprises a sequence selected from the group consisting of SEQ ID NOS: 30, 8-27, 29, 31, and 33-36 or a functional fragment and/or functional variant thereof.

In some embodiments, the aptamer comprises a sequence selected from the group consisting of SEQ ID NOS: 18-27 and wherein the sequence further comprises SEQ ID NO: 2 at the 5' end and SEQ ID NO: 5 at the 3' end.

In some embodiments, the aptamer comprises the sequence of SEQ ID NO: 30, 9, or 36.

In some embodiments, the aptamer consists of the sequence of SEQ ID NO: 30, 9, or 36.

In some embodiments, the aptamer further comprises an immobilization linker.

In some embodiments, the immobilization linker is biotin.

Also provided is an aptamer probe comprising the aptamer disclosed herein and a detectable label.

In some embodiments, the detectable label comprises a fluorescent, a colorimetric or other optical probe or electrochemical moiety.

In some embodiments, the aptamer probe comprises the sequence selected from the group consisting of SEQ ID NO: 33-35.

According to another aspect, there is provided a method for detecting the presence of eosinophil peroxidase in a sample, the method comprising:
  a) contacting the sample with the aptamer probe disclosed herein; and
  b) detecting a signal generated from binding of the aptamer with the eosinophil peroxidase;
  wherein detecting the signal indicates the presence of the eosinophil peroxidase in the sample.

In some embodiments, the method further comprises dispersing the sample in a buffer solution comprising about 2 mM dithiothreitol before step a). In some embodiments, the buffer solution comprises HEPES. In some embodiments, the buffer solution comprises about 50 mM HEPES. In some embodiments, the sample is a sputum sample.

Also provided is a method for detecting the presence of eosinophil peroxidase in a sample, the method comprising:
  a) contacting the sample with an immobilized aptamer disclosed herein in a first buffer solution;
  b) allowing the immobilized aptamer to bind to the eosinophil peroxidase to form an immobilized aptamer-eosinophil peroxidase complex
  c) transferring the immobilized aptamer-eosinophil peroxidase complex to a second buffer solution;
  d) adding a solution of $H_2O_2$ and 3,3',5,5'-tetramethyl-benzidine to the second buffer solution; and
  e) detecting a colorimetric signal;
  wherein detecting the colorimetric signal indicates the presence of eosinophil peroxidase in the sample.

In some embodiments, the method further comprises, before step c), washing the immobilized aptamer-eosinophil peroxidase complex with a washing buffer. In some embodiments, the immobilized aptamer-eosinophil peroxidase complex is washed up to 3 times before step c). In some embodiments, the method further comprises dispersing the sample in a buffer solution comprising about 2 mM dithiothreitol before step a). In some embodiments, the buffer solution comprises HEPES. In some embodiments, the buffer solution comprises about 50 mM HEPES. In some embodiments, the sample is a sputum sample.

According to another aspect, there is provided a kit for detecting eosinophil peroxidase, wherein the kit comprises the aptamer disclosed herein and instructions for use of the kit.

Also provided is a kit for detecting eosinophil peroxidase, wherein the kit comprises the aptamer probe disclosed herein and instructions for use of the kit.

According to another aspect, there is provided a use of the aptamer disclosed herein for detecting eosinophil peroxidase.

Also provided is a use of the aptamer probe disclosed herein for detecting eosinophil peroxidase.

Also provided is a use of the kit disclosed herein for detecting eosinophil peroxidase.

Other features and advantages of the present disclosure will become apparent from the following detailed description. It should be understood, however, that the detailed description and the specific examples, while indicating embodiments of the disclosure, are given by way of illustration only and the scope of the claims should not be limited by these embodiments, but should be given the broadest interpretation consistent with the description as a whole.

DRAWINGS

Certain embodiments of the disclosure will now be described in greater detail with reference to the attached drawings in which:

FIG. 1A shows the DNA library used in the selection—N40 in the DNA library represents 40 random nucleotides in the middle of the library and the fixed arms on each side represent the primer binding regions for PCR amplification (SEQ ID NO: 1).

FIG. 1B shows a schematic illustration of the in vitro selection method.

FIG. 1C shows selection of EPX-binding DNA aptamers in exemplary embodiments of the disclosure. FIG. 1C shows the top 10 sequences (SEQ ID NOs: 18-27) from both of two types of selections, including the percent of enrichment during selection.

FIG. 1D shows selection of EPX-binding DNA aptamers in exemplary embodiments of the disclosure. FIG. 1D shows dissociation constants ($K_d$) determined from electrophoretic mobility shift assays (EMSA) for each of the aptamer sequences shown in FIG. 1C.

FIG. 1E shows selection of EPX-binding DNA aptamers in exemplary embodiments of the disclosure. FIG. 1E shows binding isotherm for aptamer EAP1-05 determined from EMSA experiments.

FIG. 2A shows truncation studies of EAP1-05 and binding assays in exemplary embodiments of the disclosure. FIG. 2A shows full-length (SEQ ID NO: 9) and truncated sequences (SEQ ID NOs: 28-31) with curved dashes denoting deleted bases and light grey bases in EAP1-05T4 representing replaced bases.

FIG. 2B shows truncation studies of EAPi-05 and binding assays in exemplary embodiments of the disclosure. FIG. 2B shows single point EMSA-based binding assays of the sequences shown in FIG. 2A using 3 nM aptamer and 5 nM EPX.

FIG. 5A shows fluorescence anisotropy of EAPi-05 aptamer with EPX in PBS (white circles), 0.5×SB (black squares), and 1×SB (white triangles).

FIG. 5B shows fluorescence anisotropy of EAP1-05 aptamer with MPO in PBS (white circles), 0.5×SB (black squares), and 1×SB (white triangles).

FIG. 5C shows fluorescence anisotropy of EAP1-05T3 aptamer with EPX using the buffers listed in FIG. 5A (error bars represent the standard deviation of triplicate measurements).

FIG. 5D shows fluorescence anisotropy of EAP1-05T3 aptamer with MPO using the buffers listed in FIG. 5A (error bars represent the standard deviation of triplicate measurements).

FIG. 6A shows a schematic illustration of the EPX pull-down assay.

FIG. 6B shows images and $OD_{450}$ of quenched samples to evaluate the selectivity of the aptamer-pulldown assay.

FIG. 6C shows images and $OD_{450}$ of quenched samples to evaluate the concentration-response and limit of detection of the pulldown assay using EPX in HEPES buffer.

FIG. 6D shows images and $OD_{450}$ values of quenched samples to evaluate the concentration-response and limit of detection of the pulldown assay using EPX spiked into 25% sputum.

FIG. 8A shows that DTT/PBS buffer was not compatible with peroxidase assay.

FIG. 8B shows high amount of DTT (0.1%) used in routine clinical processing interfered with EPX reaction.

FIG. 8C shows a

5

6 reduction of DTT to 2 mM in HEPES buffer (HB) produced the required dispersal of the sputum sample while retaining the ability to generate a color from the aptamer-based peroxidase assay.

Figure 9:
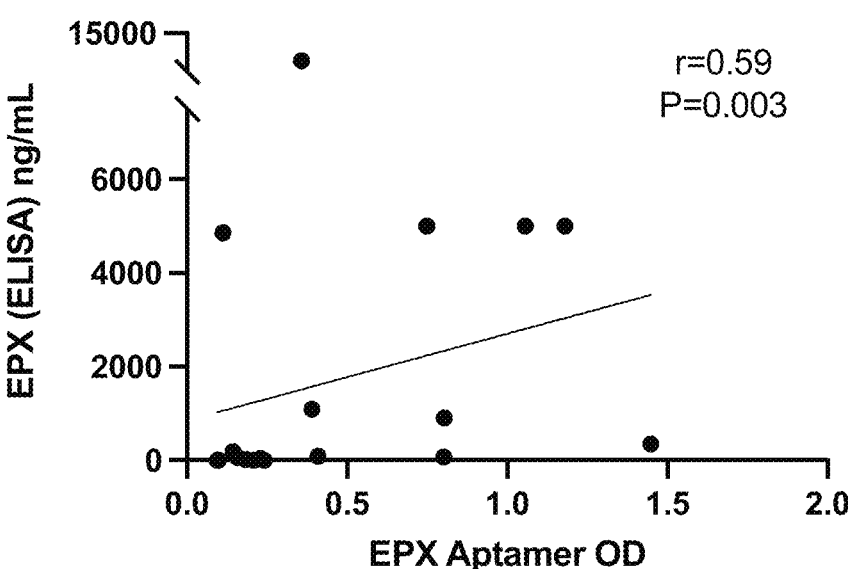

FIG. 9 shows a correlation plot for EPX aptamer values with EPX ELISA in HEPES buffer-dispersed sputum samples in exemplary embodiments of the disclosure.

Figure 10A:
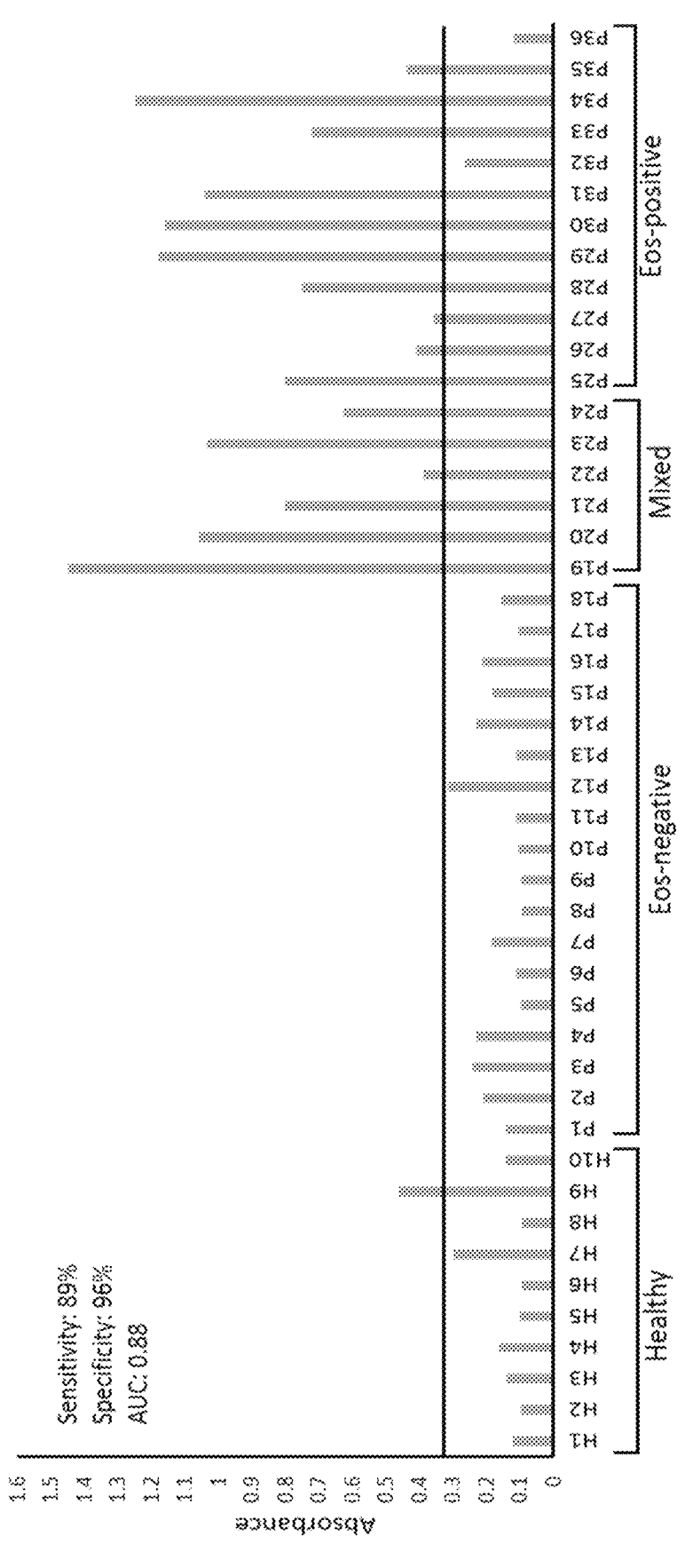

FIG. 10A shows evaluation of EPX pulldown assay with subjects' sputum samples in exemplary embodiments of the disclosure. FIG. 10A shows OD values of EPX pulldown assay for a total of 46 clinical samples.

FIG. 10B shows evaluation of EPX pulldown assay with subjects' sputum samples in exemplary embodiments of the disclosure. FIG. 10B shows images of colorimetric outputs for healthy samples.

FIG. 10C shows evaluation of EPX pulldown assay with subjects' sputum samples in exemplary embodiments of the disclosure. FIG. 10C shows images of colorimetric outputs for negative samples.

FIG. 10D shows evaluation of EPX pulldown assay with subjects' sputum samples in exemplary embodiments of the disclosure. FIG. 10D shows images of colorimetric outputs for mixed samples.

FIG. 10E shows evaluation of EPX pulldown assay with subjects' sputum samples in exemplary embodiments of the disclosure. FIG. 10E shows images of colorimetric outputs for positive samples.

Figure 11:
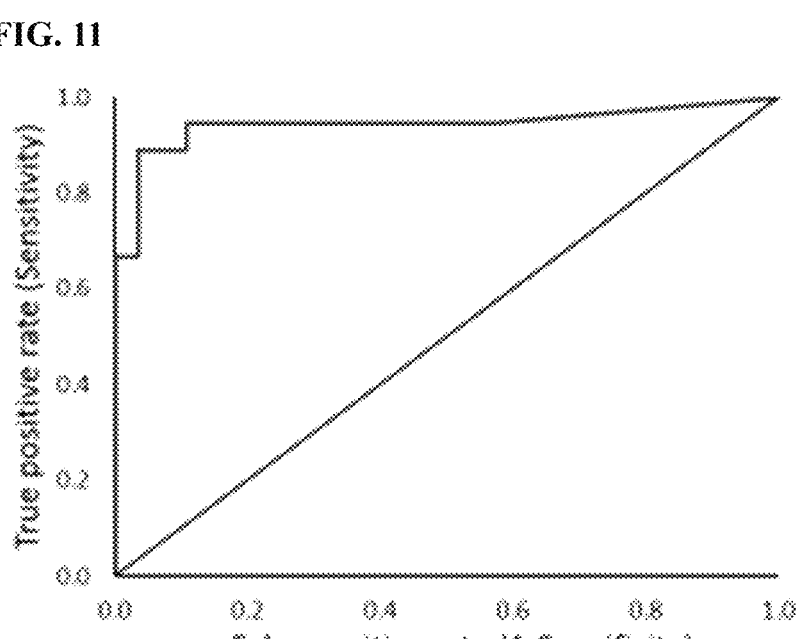

FIG. 11 shows a Receiver-Operator Characteristics (ROC) plot for the pulldown assay data from FIG. 9 in exemplary embodiments of the disclosure.

Figure 12A:
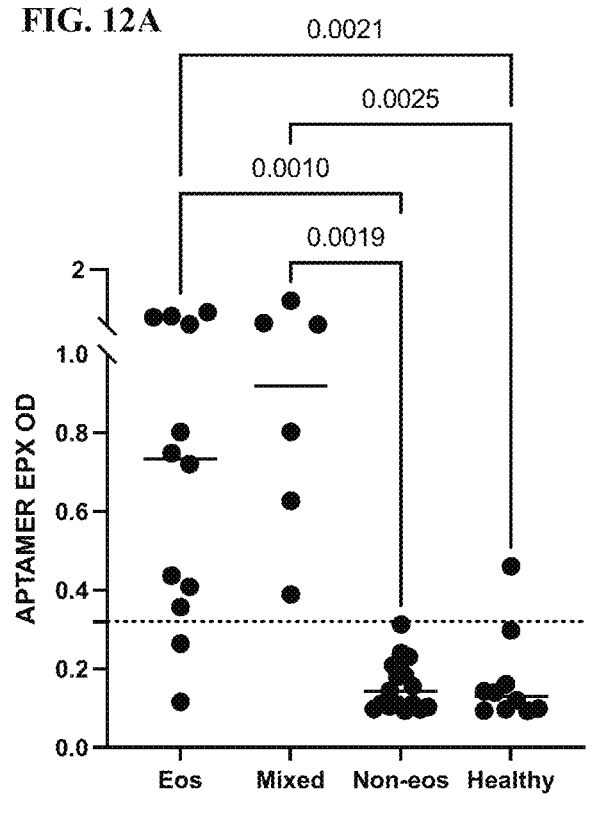

FIG. 12A shows statistical analysis of clinical validation and correlation data for the assay in exemplary embodiments of the disclosure. FIG. 12A shows scatter plots showing distribution of aptamer EPX OD data for eosinophilic, mixed granulocytic (evidence of eosinophilia and neutrophils) and non-eosinophilic samples (negative) samples— the cut-off value 0.32 was assessed based on the AUC (receiver-operating curve) using values generated from n=18 negative samples from FIG. 10; negative samples were confirmed by absence of eosinophils and free eosinophil granules using gold standard (routine sputum cytology).

Figure 12B:
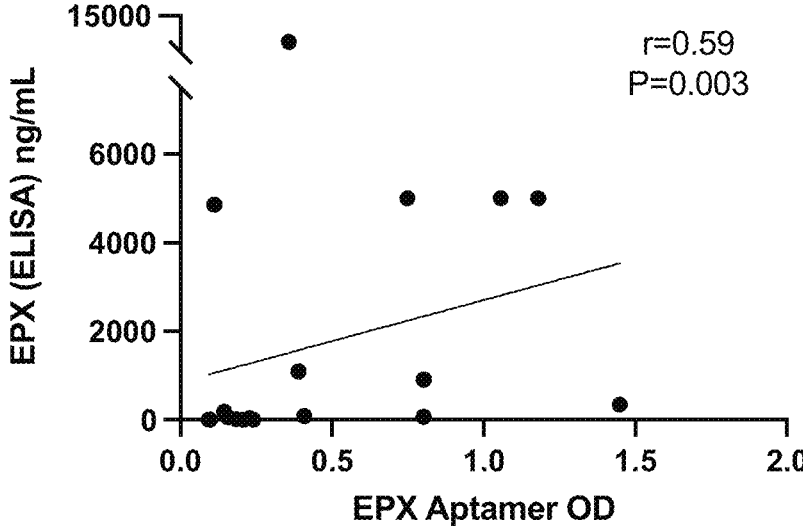

FIG. 12B shows statistical analysis of clinical validation and correlation data for the assay in exemplary embodiments of the disclosure. FIG. 12B shows correlation between aptamer assay OD values and percent eosinophils present in sputum samples.

Figure 12C:
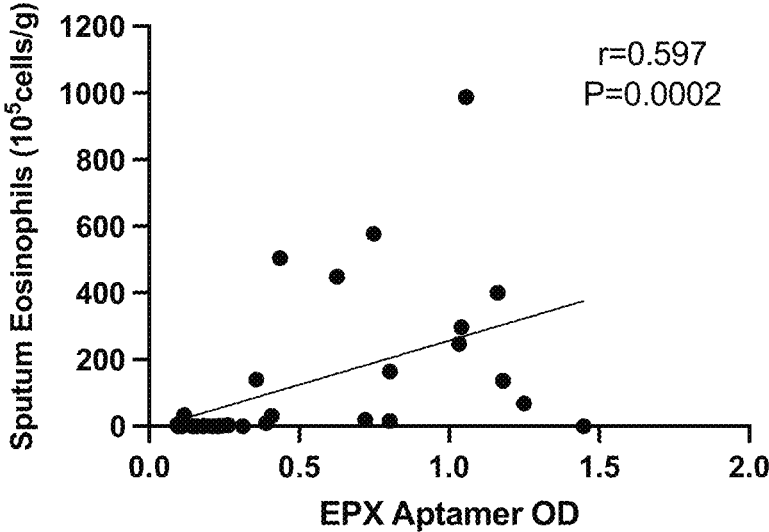

FIG. 12C shows statistical analysis of clinical validation and correlation data for the assay in exemplary embodiments of the disclosure. FIG. 12C shows correlation between aptamer assay OD values and total eosinophils present in sputum samples (each symbol is representative one patient/ individual value using Kruskal Wallis and Spearman correlation test; $P < 0.05$ considered as significant).

Figure 13:
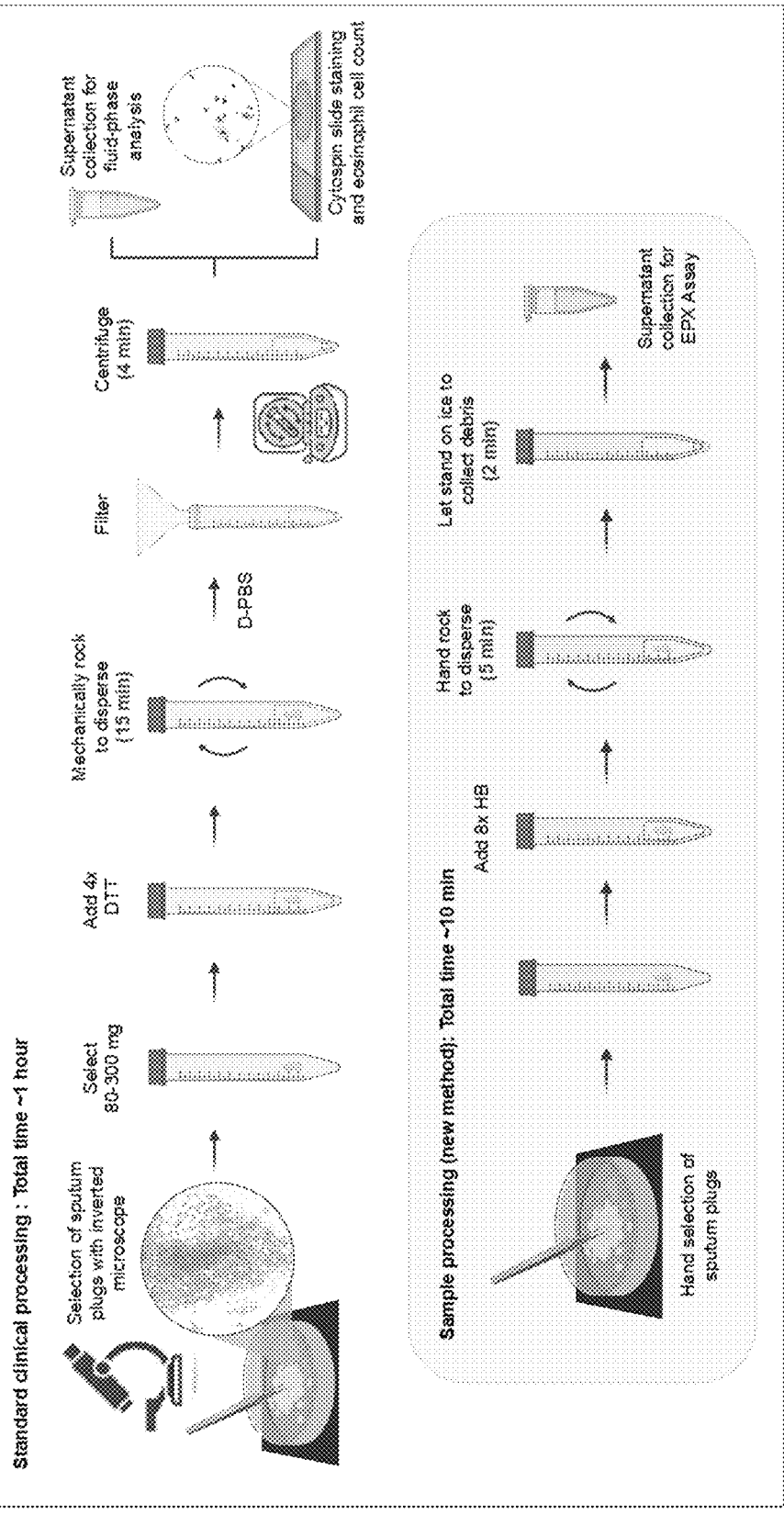

FIG. 13 shows comparison of sputum sample processing steps for the conventional method (top) and the method of the present disclosure (bottom) in exemplary embodiments of the disclosure. FIG. 13 shows the reduction in the number of steps and technical complexity for the new sample processing method.

Figure 14:
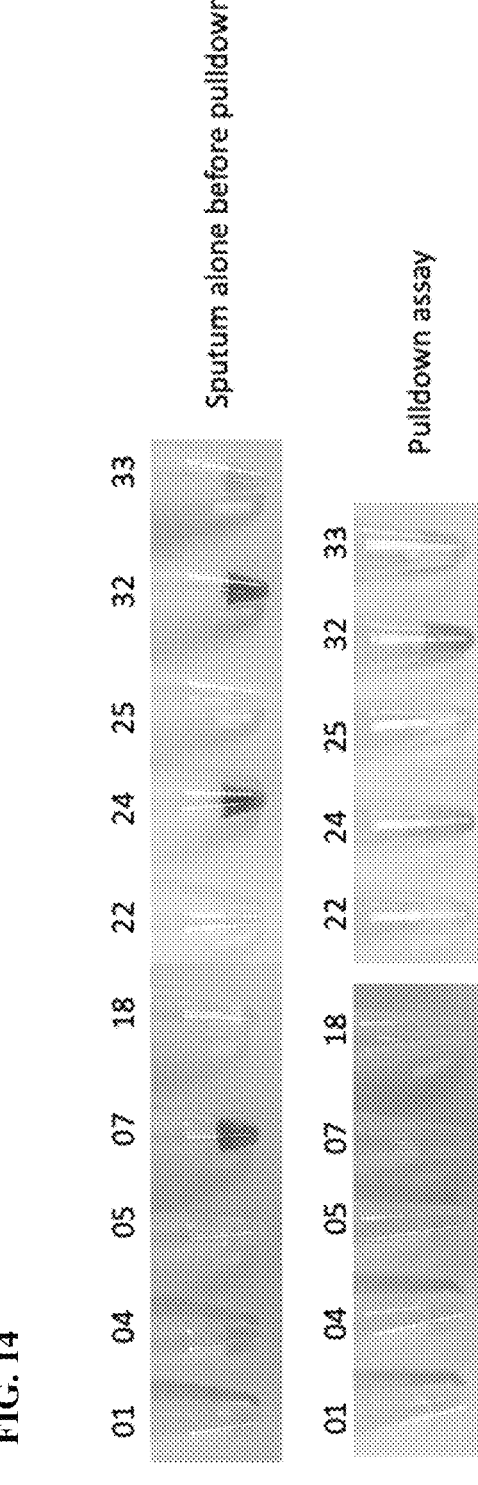

FIG. 14 shows visual output of peroxide/TMB assay for processed sputum prior to performing the aptamer pulldown assay on 10 healthy sputum samples.

DETAILED DESCRIPTION

I. Definitions

Unless otherwise indicated, the definitions and embodiments described in this and other sections are intended to be applicable to all embodiments and aspects of the present disclosure herein described for which they are suitable as would be understood by a person skilled in the art. It is also to be understood that the terminology used herein is for the purpose of describing particular aspects only and is not intended to be limiting.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies. In addition, all ranges given herein include the end of the ranges and also any intermediate range points, whether explicitly stated or not.

As used in this disclosure, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The abbreviation, "e.g." is derived from the Latin exempli gratia and is used herein to indicate a non-limiting example. Thus, the abbreviation "e.g." is synonymous with the term "for example." The word "or" is intended to include "and" unless the context clearly indicates otherwise.

The term "room temperature" as used herein refers to a temperature in the range of about 20° C. and about 25° C.

The term "sample" or "test sample" as used herein refers to any material in which the presence or amount of a target analyte is unknown and can be determined in an assay or a method. The sample can be from any source, for example, any biological (e.g. human or animal samples, including clinical samples), environmental (e.g. water, soil or air) or natural (e.g. plants) source, or from any manufactured or synthetic source (e.g. food or drinks). The sample can be comprised or is suspected of comprising one or more analytes. The sample can be a "biological sample" comprising cellular and non-cellular material, including, but not limited to, tissue samples, saliva, sputum, urine, blood, serum, other bodily fluids and/or secretions. In some embodiments, the sample comprises saliva, sputum, oropharyngeal and/or nasopharyngeal secretions.

The term "target", "analyte" or "target analyte" as used herein refers to any agent, including, but not limited to, a small inorganic molecule, small organic molecule, metal ion, biomolecule, toxin, biopolymer (such as a nucleic acid, carbohydrate, lipid, peptide, protein), cell, tissue, microorganism and virus, for which one would like to sense or detect. The analyte can be either isolated from a natural source or synthetic. The analyte can be a single compound or a class of compounds, such as a class of compounds that share structural or functional features. The term analyte also includes combinations (e.g. mixtures) of compounds or agents such as, but not limited, to combinatorial libraries and samples from an organism or a natural environment.

The term "nucleic acid" as used herein refers to a biopolymer comprising monomers of nucleotides, such as deoxyribonucleic acid (DNA), ribonucleic acid (RNA) and other polynucleotides of modified nucleotides and/or nucleotide derivatives, and can be either double stranded (ds) or single stranded (ss). In some embodiments, modified nucleotides can contain one or more modified bases (e.g. unusual bases such as inosine, and functional modifications to the bases such as amino), modified backbones (e.g. peptide nucleic acid, PNA) and/or other chemically, enzymatically, or metabolically modified forms.

The term "aptamer" as used herein refers to a short, chemically synthesized nucleic acid molecule or oligonucleotide sequence which can be generated by in vitro selection to fold into specific three-dimensional structures that bind to a specific analyte with dissociation constants, for example, in the pico- to nano-molar range. Aptamers can be single-stranded DNA, and include RNA, modified nucleotides and/or nucleotide derivatives. Aptamers can also be naturally occurring RNA aptamers termed "riboswitches". Functional aptamer sequences can also be rationally designed, truncated, conjugated or otherwise modified from original parent (or full length) sequences.

It will be understood that any component defined herein as being included can be explicitly excluded by way of proviso or negative limitation, such as any specific compounds or method steps, whether implicitly or explicitly defined herein.

II. Compositions and Methods of the Disclosure

Disclosed herein is the in vitro selection and improvement of DNA aptamers that bind to eosinophil peroxidase (EPX), a protein biomarker unique to eosinophils. 15 rounds of magnetic bead aptamer selection were performed prior to high throughput DNA sequencing. The top 10 aptamer candidates were assessed for EPX binding using a mobility shift assay. This process identified a lead aptamer candidate, termed EAP1-05 herein, with low nanomolar affinity and high specificity for EPX over other common sputum proteins. In some embodiments, this aptamer sequence was further improved through truncation and used to develop an easy-to-use colourimetric pull-down assay that allows eosinophilia monitoring without using sophisticated equipment. In further embodiments, a sputum processing method was developed such that the assay was utilized for the detection of EPX in 46 clinical samples and showed 89% sensitivity and 96% specificity, with results being produced in under an hour. Both the DNA aptamers and sputum-based bioassay allow for rapid testing of eosinophils as an easy assessment of eosinophil activity in the airway, which can aid in the diagnosis of airway disorders associated with eosinophilia and help guide specific therapies against eosinophils, such as anti-inflammatory therapy for several airway diseases.

Accordingly, provided is a DNA aptamer that binds eosinophil peroxidase, wherein the aptamer comprises a sequence selected from the group consisting of SEQ ID NOS: 30, 8-27, 29, 31, and 33-36 or a functional fragment and/or functional variant thereof.

In some embodiments, the aptamer comprises a sequence selected from the group consisting of SEQ ID NOS: 18-27 and wherein the sequence further comprises SEQ ID NO: 2 at the 5' end and SEQ ID NO: 5 at the 3' ends.

In some embodiments, the aptamer comprises the sequence of SEQ ID NO: 9, 29-31, or 36. In some embodiments, the aptamer comprises the sequence of SEQ ID NO: 30, 9, or 36. In some embodiments, the aptamer comprises the sequence of SEQ ID NO: 30. In some embodiments, the aptamer comprises the sequence of SEQ ID NO: 36.

In some embodiments, the aptamer consists of the sequence of SEQ ID NO: 9, 29-31, or 36. In some embodiments, the aptamer consists of the sequence of SEQ ID NO: 30, 9, or 36. In some embodiments, the aptamer consists of the sequence of SEQ ID NO: 30. In some embodiments, the aptamer consists of the sequence of SEQ ID NO: 36.

In some embodiments, the aptamer binds eosinophil peroxidase with at least nanomolar affinity.

In some embodiments, the aptamer further comprises an immobilization linker. In some embodiments, the immobilization linker comprises a natural or synthetic linker. In some embodiments, the aptamer is immobilized on a support. In some embodiments, the support is a solid or semi-solid support. In some embodiments, the support comprises cellulose or paper.

In some embodiments, the immobilization linker is biotin. In some embodiments, the biotin acts as a linker via biotin-streptavidin interactions.

Also provided is an aptamer probe comprising the aptamer disclosed herein and a detectable label.

In some embodiments, the detectable label comprises a fluorescent, a colorimetric or other optical probe or electrochemical moiety. In some embodiments, the detectable label comprises a fluorescent moiety, such as a fluorophore. In some embodiments, the detectable label comprises fluorescein amidites (FAM). In some embodiments, the aptamer probe is immobilized on a support. In some embodiments, the support is a solid or semi-solid support. In some embodiments, the support comprises cellulose or paper.

In some embodiments, the aptamer probe comprises the sequence selected from the group consisting of SEQ ID NO: 33-35.

Also provided herein is an assay for detecting the presence of eosinophil peroxidase comprising:
   a) the aptamer disclosed herein immobilized on and/or in a material in a buffer solution;
   b) a solution comprising $H_2O_2$ and 3,3',5,5'-tetramethylbenzidine;
   wherein binding of the immobilized aptamer to the eosinophil peroxidase results in production of a colorimetric signal.

In some embodiments, the aptamer is directly or indirectly immobilized on and/or in a material. In some embodiments, the aptamer is immobilized on a surface of the material. In some embodiments, the aptamer is directly linked to the material. In some embodiments, the linker comprises a thiol. In some embodiments, the aptamer is indirectly linked to the material. In some embodiments, the linker is a biotin. In some embodiments, the biotin links the aptamer to the material via biotin-streptavidin interactions.

In some embodiments, the material comprises microscale or nanoscale particles, such as but not limited to, gold nanoparticles, agarose beads or magnetic beads. In some embodiments, the material comprises agarose beads.

Also provided is a method for detecting the presence of eosinophil peroxidase in a sample, the method comprising:

a) contacting the sample with the aptamer probe disclosed herein; and b) detecting a signal generated from binding of the aptamer with the eosinophil peroxidase;

wherein detecting the signal indicates the presence of the eosinophil peroxidase in the sample.

In some embodiments, the method further comprises dispersing the sample in a buffer solution comprising about 2 mM dithiothreitol before step a). In some embodiments, the buffer solution comprises HEPES. In some embodiments, the buffer solution comprises about 50 mM HEPES. In some embodiments, the buffer solution comprises 50 mM HEPES and 300 mM NaCl. In some embodiments, the buffer solution comprises 50 mM HEPES, 300 mM NaCl, 15 mM MgCl2, 0.01% Tween20, at pH 7.5. In some embodiments, the sample is a sputum sample.

Also provided herein is a method for detecting the presence of eosinophil peroxidase in a sample, the method comprising:

a) contacting the sample with an immobilized aptamer disclosed herein in a first buffer solution;

b) allowing the immobilized aptamer to bind to the eosinophil peroxidase to form an immobilized aptamer-eosinophil peroxidase complex c) transferring the immobilized aptamer-eosinophil peroxidase complex to a second buffer solution;

d) adding a solution of $H_2O_2$ and 3,3',5,5'-tetramethylbenzidine to the second buffer solution; and e) detecting a colorimetric signal;

wherein detecting the colorimetric signal indicates the presence of eosinophil peroxidase in the sample.

In some embodiments, the aptamer is directly or indirectly immobilized on and/or in a material. In some embodiments, the aptamer is immobilized on a surface of the material. In some embodiments, the aptamer is directly linked to the material. In some embodiments, the linker comprises a thiol. In some embodiments, the aptamer is indirectly linked to the material. In some embodiments, the linker is a biotin. In some embodiments, the biotin links the aptamer to the material via biotin-streptavidin interactions. In some embodiments, the material comprises microscale or nanoscale particles. In some embodiments, the microscale or nanoscale particles comprise gold nanoparticles, agarose beads or magnetic beads. In some embodiments, the material comprises agarose beads.

In some embodiments, the method further comprises, before step c), washing the immobilized aptamer-eosinophil peroxidase complex with a washing buffer. In some embodiments, the immobilized aptamer-eosinophil peroxidase complex is washed up to 3 times before step c). In some embodiments, the immobilized aptamer-eosinophil peroxidase complex is washed at least 3 times and up to 5 times. In some embodiments, the washing buffer comprises PBS. In some embodiments, the method further comprises dispersing the sample in a buffer solution comprising about 2 mM dithiothreitol before step a). In some embodiments, the buffer solution comprises HEPES. In some embodiments, the buffer solution comprises about 50 mM HEPES. In some embodiments, the buffer solution comprises about 50 mM HEPES. In some embodiments, the buffer solution comprises 50 mM HEPES and 300 mM NaCl. In some embodiments, the buffer solution comprises 50 mM HEPES, 300 mM NaCl, 15 mM MgCl2, 0.01% Tween20, at pH 7.5.

In some embodiments, the sample is a sputum sample. In some embodiments, the sputum is separated from saliva in the sample. In some embodiments, the sputum is separated from saliva in the sample using forceps.

Also provided is a kit for detecting eosinophil peroxidase, wherein the kit comprises the aptamer or the aptamer probe disclosed herein and instructions for use of the kit. In some embodiments, the aptamer or the aptamer probe is an immobilized aptamer. In some embodiments, the aptamer or the aptamer probe is directly or indirectly immobilized on and/or in a material. In some embodiments, the aptamer or the aptamer probe is immobilized on a surface of the material. In some embodiments, the aptamer or the aptamer probe is directly linked to the material. In some embodiments, the linker comprises a thiol. In some embodiments, the aptamer or the aptamer probe is indirectly linked to the material. In some embodiments, the linker is a biotin. In some embodiments, the biotin links the aptamer to the material via biotin-streptavidin interactions. In some embodiments, the material comprises microscale or nanoscale particles. In some embodiments, the microscale or nanoscale particles comprise gold nanoparticles, agarose beads or magnetic beads. In some embodiments, the material comprises agarose beads.

In some embodiments, the kit further comprises one or more buffers. In some embodiments, the aptamer or the aptamer probe is immobilized on a material in a buffer solution. In some embodiments, the aptamer or the aptamer probe is immobilized in a material in a buffer solution. In some embodiments, the kit further comprises a solution comprising $H_2O_2$ and 3,3',5,5'-tetramethylbenzidine. In some embodiments, the kit further comprises a washing buffer. In some embodiments, the washing buffer comprises PBS.

In some embodiments, the kit further comprises a buffer solution for dispersing a sample. In some embodiments, the buffer solution comprising about 2 mM dithiothreitol. In some embodiments, the buffer solution comprises HEPES. In some embodiments, the buffer solution comprises about 50 mM HEPES. In some embodiments, the buffer solution comprises about 50 mM HEPES. In some embodiments, the buffer solution comprises 50 mM HEPES and 300 mM NaCl. In some embodiments, the buffer solution comprises 50 mM HEPES, 300 mM NaCl, 15 mM MgCl2, 0.01% Tween20, at pH 7.5.

Also provided herein is a use of the aptamer, the aptamer probe, the assay, or the kit disclosed herein for detecting eosinophil peroxidase.

EXAMPLES

The following non-limiting examples are illustrative of the present disclosure:

Methods

Oligonucleotides and chemicals: All DNA oligonucleotides (Table 1) were obtained from Integrated DNA Technologies (Iowa, USA), and purified by standard 10% dPAGE (7M urea) prior to use. NHS-Activated Magnetic beads (Prod. #88826) and Pierce streptavidin-coated agarose beads (Prod. #20349) were purchased from Thermo Scientific (Burlington, Ontario). Biotools DNA polymerase (#BTL- 10043) was purchased from Mandel Scientific (Guelph, Ontario). Eosinophil peroxidase (EPX, #342-60-0.1), Myeloperoxidase (MPO, #426-10-0.1), Thyroid peroxidase (TPO, #ABIN934717) and Lactoperoxidase (LPO, #LS000151) were purchased from Cedarlane (Burlington, Ontario). Enhanced K-blue TMB substrate was from Neogen (#308175, KY, USA). Streptavidin-agarose beads were purchased from Thermo Fisher Canada. Buffers are outlined in Table 2. All other chemicals were purchased from Sigma-Aldrich and used without further purification.

Instruments: A Tecan M1000 plate reader was used for microplate fluorescence readings at an excitation wavelength of 490 nm and emission at 520 nm, with the exception of fluorescence anisotropy which was limited to a filter using excitation at 470 nm and emission at 520 nm. PCR was performed using a Dual 48 Bio-Rad thermal cycler. Agarose gels were visualized using a Bio-Rad ChemiDoc imaging system and quantified using Image Lab 6.0 software. Pictures of the microwell plates and microcentrifuge tubes used in the EPX pulldown assay were taken using a LG G5 or Samsung Galaxy S9 cellular phone operated in automatic mode. FIG.s were made using GraphPad Prism 5 or Excel 2016 software.

Conjugating EPX/MPO to magnetic beads: Proteins were coupled to the magnetic beads (MBs) as per the manufacturer's protocol. Briefly, 300 μL of MBs were mixed with Cwb A (see buffer composition in Table 2) for 15 seconds, then placed in a magnetic stand to collect the beads and discard the supernatant. EPX (for positive selection) or MPO (for counter selection) was then added and mixed on a 3600 microfuge tube rotator for two hours at room temperature. After brief centrifugation using benchtop centrifuge machine, the MBs were separated with a magnetic stand and the supernatant was saved for quantification of unbound protein via Bradford assay. The MBs were washed with 500 μL of Cwb B for 15 seconds, then the supernatant was discarded. This washing with Cwb B was repeated two more times, followed by two washes with ddH$_2$O. Qb was then added for two hours to quench any unreacted amine moieties, followed by three washes with ddH$_2$O. The beads were suspended in SB and kept at 4° C. until use.

In vitro aptamer selection: The selection protocol was adapted from two previous reported protocols and is outlined in FIG. 1B.[1,2] Both EPX- and MPO-coated MBs were washed 5×using 1×WB prior to use. One nanomole of DNA library (DNA$_L$) was dissolved in 50 μL of 1×SB, heated at 90° C. for 5 minutes then cooled at room temperature for 20 minutes. This solution was added to 500 μL of MPO-coated MBs suspended in 1×SB, mixed and incubated at room temperature for 30 minutes with mild shaking. The MBs were separated by a magnetic separator and the unbound free DNA molecules in the clear supernatant were collected. These unbound DNA molecules in the supernatant were then added to the suspension of EPX-coated MBs for positive selection (500 μL volume, approximately 50 pmol of EPX) and incubated at room temperature with mild shaking for 2 hours. Then, the MBs were separated by magnetic separator and the supernatant was discarded. The MBs were washed 9× using 1×WB (500 μL each). After washing, the bound DNA molecules were eluted from the beads by heating the beads at 80° C. for 40 minutes in 300 μL elution buffer (EB). The DNA molecules in EB was then precipitated by standard ethanol precipitation and resuspended in 50 μL of ddH$_2$O. One microliter of this DNA solution was used in PCR amplification.

The PCR was conducted in 50 μL volume in two steps with two sets of primers called PCR1 and PCR2.[3] The PCR1 mixture contained 1 μL of the eluted DNA from the positive selection along with 1 μM FP1, 1 μM RP1, 200 mM dNTPs, 1×PCR reaction buffer (75 mM Tris-HCl, 2 mM MgCl2, 50 mM KCl, 20 mM (NH$_4$)$_2$SO$_4$, pH 9), and 2.5 U Biotools DNA polymerase. Thermal cycles were performed as follows: 95° C. for 60 seconds; ~15-18 cycles of 90° C. for 45 seconds, 53° C. for 45 seconds, 70° C. for 45 seconds and finally 5 min incubation at 70° C. for extension. PCR product was analyzed by agarose gel electrophoresis (2% w/v containing 1×SYBR GOLD) to ensure sufficient PCR product. A portion of PCR1 product was diluted 20× and 1 μL of this diluted PCR1 product was applied in PCR2 in 50 μL with the same condition of PCR1 except using FP2 and RP2 primer set. The triethylene glycol spacer in RP2 prevents the amplification of the poly-A region of RP2, resulting in the aptamer sequence being 20 nucleotides shorter than the antisense strand. The aptamer was purified using denaturing dPAGE and used in the next round of selection in the same way as described for the first round of selection. The selection and enrichment by PCR were iterated until round seven. In round seven, the DNA pool was divided into two. The same selection was continued with the first portion, while the second portion was applied in a modified selection protocol wherein the EPX-coupled MBs were blocked by adding 1 μM blocker DNA before adding the purified DNA$_L$ of round seven. Both selections were continued until 15 rounds and the DNA population of each selection was employed in deep sequencing (McMaster University, DNA sequencing facility). The amount of MBs and DNA pool of each round of selection can be found in Table 3.

Electrophoretic mobility shift assay (EMSA): The EPX binding of the top 5 aptamers from each selection were analyzed by EMSA. Binding reactions were performed in 10 μL of 1×SB containing 3 nM fluorescently labelled DNA, 1 ng poly(dI-dC) and target protein (concentrations ranging from 0-100 nM). After binding for 60 minutes, 10 μL of native loading buffer (1×SB+40% w/v sucrose) was added and the samples were loaded into a 0.3% w/v agarose gel. The gel was visualized and analyzed by Bio-Rad Chemi-doc™ imager.

Anisotropy of DNA/protein interactions: Fluorescence anisotropy was performed in 50 μL reactions containing 3 nM aptamer in buffer (PBS, 0.5×SB, or 1×SB) and protein (EPX or MPO) ranging from 0-100 nM. A G-factor of 1.105 was determined by calibrating the fluorimeter with 1 nM fluorescein in 10 mM NaOH, and used to correct for the polarization bias of the system. All samples were prepared in duplicate, then measured in triplicate after reacting for 60 minutes at room temperature.

EPX pulldown assay: Biotinylated EAP1-05T3 was immobilized on streptavidin-coated agarose beads as follows: 200 μL of streptavidin-coated agarose slurry was transferred into a 1.5 mL Eppendorf tube and washed with 500 μL of 1×HB (50 mM HEPES, 300 mM NaCl, 15 mM MgCl2, 0.01% Tween20, pH 7.5). 1 nmole of biotinylated EAP1-05T3 was added to this slurry and rotated gently for 1 h to bind the aptamers with the beads. The beads were washed 5× with 500 μL of 1×1B each time and finally suspended in 1000 μL of 1× HB and stored at 4° C. until use. 50 μL of this bead slurry was used for each pull-down experiment.

Specificity test: 50 μL of aptamer-conjugated beads from above were aliquoted in each tube and labelled for each experiment: Buffer, EPX, MPO, LPO, TPO and BSA respectively. 1 μM stock of each of protein was made in 1×HB. Next, 1.0 μL of each protein was added to their respected tube and incubated at room temperature for 30 minutes with occasional pipetting for homogeneous binding. Only buffer was added in the control experiment tube that was labelled as buffer. Then the beads were sedimented by brief centrifugation using a benchtop centrifuge and washed 3× using 300 μL 1×HB. Next, the beads were resuspended in 25 μL HB. 35 μL of TMB solution (Neogen's Enhanced K-blue substrate) was added to each tube. After pipette mixing, the tubes were kept at room temperature for color development. Color was captured by smart cell phone at 5 min. Then, 70 μL of 0.5 M HCl was added to the tube to quench the peroxidase reaction. This yellow solution was immediately transferred into 96 well plate and the OD was measured at 450 nm using Tecan plate reader. The data was processed using Microsoft excel software.

Sensitivity test in buffer: EPX stocks of different concentrations (10.0, 5.0, 2.5, 1.25, 0.625, 0.312, 0.156, 0.078, 0.039 and 0.019 μM) were made in 1×HB. Similar to specificity test, 50 μL of aptamer conjugated beads slurry was transferred in each fresh Eppendorf tube (3 tubes for each concentration for triplicate experiments). 1.0 μL of each protein was added to their respected tube and incubated at room temperature for 30 minutes with occasional pipetting for homogeneous binding. Only buffer was added in the control experiment tube that was labelled as buffer. Then the beads were sedimented by brief centrifugation using a benchtop centrifuge and washed 3× using 300 μL 1××HB. Next, the beads were resuspended in 25 μL HB. 35 μL of TMB solution (Neogen's Enhanced K-blue substrate) was added to each tube. After pipette mixing, the tubes were kept at room temperature for color development. Color was captured by smart cell phone at 5 min. Then, 70 μL of 0.5 M HCl was added to the tube to quench the peroxidase reaction. This yellow solution was immediately transferred into 96 well plate and the OD was measured at 450 nm using a Tecan plate reader. The data was processed using Microsoft excel software.

Sensitivity test in sputum: Similar to the sensitivity test in buffer, EPX stocks of different concentrations (10.0, 5.0, 2.5, 1.25, 0.625, 0.312, 0.156, 0.078, 0.039 and 0.019 μM) were made in HB. The beads were suspended in HB including 20% sputum sample. 50 μL of aptamer conjugated beads slurry was transferred in each fresh Eppendorf tube (3 tubes for each concentration for triplicate experiments). 1.0 μL of protein from each stock was added to their respected tube and incubated at room temperature for 30 minutes with occasional pipetting for homogeneous binding. Only buffer was added in the control experiment tube that was labelled as buffer. Then the beads were sedimented by brief centrifugation using a benchtop centrifuge and washed 3× using 300 μL 1xx HB. Next, the beads were resuspended in 25 μL HB. 35 μL of TMB solution (Neogen's Enhanced K-blue substrate) was added to each tube. After pipette mixing, the tubes were kept at room temperature for color development. Color was captured by smart cell phone at 5 min. Then, 70 μL of 0.5 M HCl was added to the tube to quench the peroxidase reaction. This yellow solution was immediately transferred into 96 well plate and the OD was measured at 450 nm using a Tecan plate reader. The data was processed using Microsoft excel software.

Sample processing for pultdown assay of clinical samples (old method): Sputum samples were collected with the consent of each patient. The collected sputum was transferred in a fresh petri dish by pipette and put under an inverted microscope. The sputum was selected based on the cell morphology and separated. This desired sputum was then transferred in a pre-weighed 15 mL conical tube and the total amount of sputum was calculated by deducting the tube weight. Next, the sputum was dispersed by adding 8× of the PBS (137 mM NaCl, 2.7 mM KCl. 10 mM $Na_2HPO_4$, 1.8 mM $KH_2PO_4$, pH 7.4 including 4 mM DTT) and gently inverting the tube. The samples were then aliquoted 250 μL in fresh Eppendorf tubes and stored at −20° C. until use.

Sample processing for pulldown assay of clinical samples (new method): Sputum samples were collected with the consent of each patient. The sputum of each person was first put on black paper in a petri dish. If the sputum was too thick, forceps were used to select the sputum without the help of a microscope. The sputum was then transferred to a pre-weighed fresh conical 15 mL tube. The amount of sputum was calculated by deducting the tube weight. Next, the sputum was dispersed by adding 8× of the HB (50 mM HEPES, 300 mM NaCl, 15 mM MgCl2, 0.01% Tween20 pH 7.5 including 2 mM DTT) and gently inverting the tube. The samples were dispersed by inverting the tube by hand for 5 min and then settling the dispersal on ice for 2 min. The supernatants from the settled dispersed samples were then aliquoted into 250 μL in fresh Eppendorf tubes that included a protease inhibitor cocktail (Roche catalogue number 11697498001, containing a mixture of serine, cysteine and metalloproteases −1 tablet is dissolved in 50 mL deionized water as per manufacturer's protocol and 10 μL is added to 500 μL of dispersed supernatants) and stored at −20° C. until use. All reported sputa were collected using this method in addition to the above routine old method.

Aptamer pull-down assay: The stock of aptamer agarose beads was prepared in the same way as described for the spiked sputum samples. 50 μL of the aptamer-bead conjugate was transferred to a fresh microcentrifuge tube. 50 μL of the above processed sample was added to this tube and mixed. The tube was rotated vertically to prevent the beads from settling down. After 30 min of incubation, the tube was briefly centrifuged to separate the beads. The supernatant was carefully discarded. The beads were washed three times (300 μL in each wash) with HB. The beads were then suspended in 25 μL of HB. This was followed by the addition of 35 μL of TMB solution (Neogen's ready-to-use K-blue ready substrate) and allowed to develop color. The color was captured at 5 min using a smart phone. Then, 70 μL of 0.5 M HCl was added to the tube to quench the peroxidase reaction. This yellow solution was immediately transferred to a 96 well plate and the OD was measured at 450 nm using a Tecan plate reader. The data was processed using Microsoft excel software.

Results and Discussion

Figure 1A:
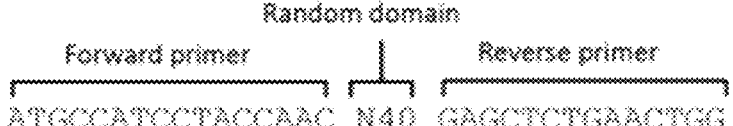
FIG. 1A shows selection of EPX-binding DNA aptamers in exemplary embodiments of the disclosure.
Figure 1B:
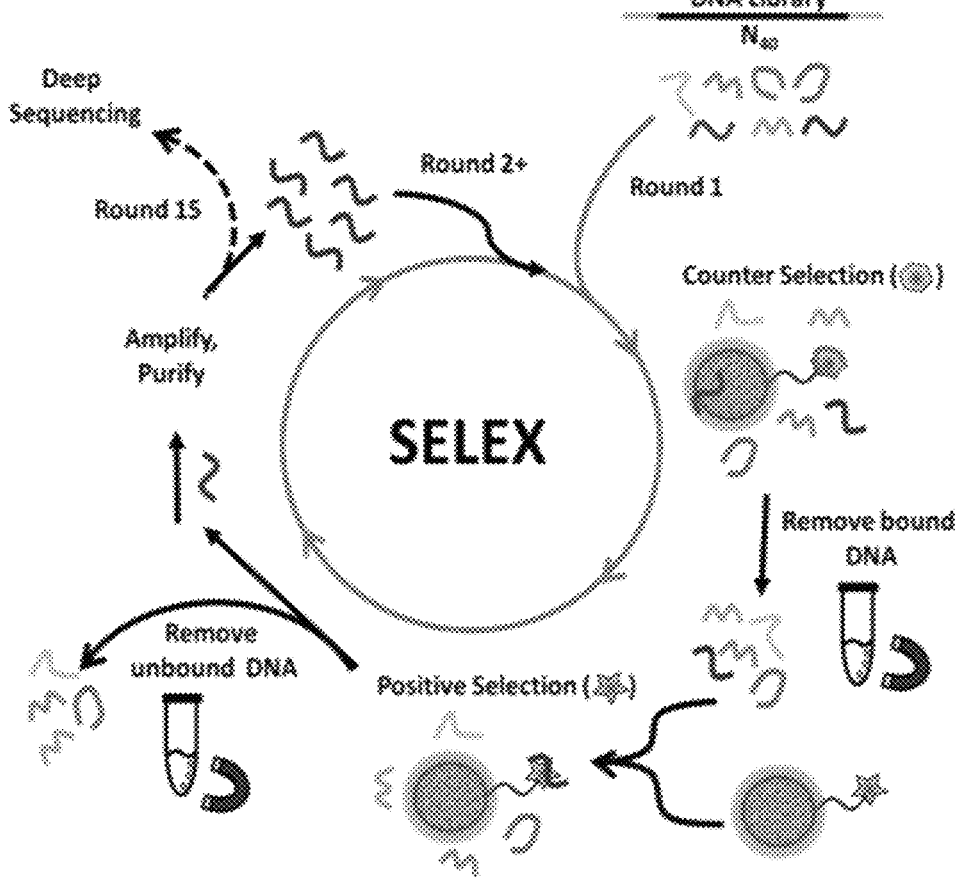
FIG. 1B shows selection of EPX-binding DNA aptamers in exemplary embodiments of the disclosure.

To identify DNA aptamers for EPX, SELEX experiments were carried out using magnetic beads (MB) with immobilized EPX and a DNA library ($DNA_L$) containing 40 random nucleotides, the random domain (RD), flanked by fixed domains in each end to serve as PCR primer binding arms (FIG. 1A; see Table 1 for the sequences of all oligonucleotides used in this disclosure). The protocol used for the selection experiments is shown in FIG. 1B. Briefly, either EPX (for positive selection) or myeloperoxidase (MPO, for negative selection) were covalently conjugated to N-hydroxysuccinimide-activated magnetic beads following the manufacturer's instructions. The selection process began with a negative selection wherein the $DNA_L$ was incubated with the MPO-coated MBs. After incubation, the MBs were magnetically separated and the unbound free DNA sequences in the supernatant were collected, amplified by PCR to the reach the original concentration of the library, and employed in the positive selection with EPX-coated beads. In the positive selection, the unbound free sequences were discarded. After washing the beads, the bound DNA molecules were dissociated from the bead, isolated, and amplified by PCR. The sense strands of the PCR products were then purified by denaturing polyacrylamide gel electrophoresis (dPAGE) and employed in the next round of negative selection. Since EPX is a highly cationic protein, the selection was conducted in a buffer with a high pH (9.0) and high salt concentration (1.0 M NaCl) to reduce the non-specific electrostatic interactions between EPX and $DNA_L$. To further improve the specific binding of the DNA pool with EPX, the PCR product of round seven was divided into two pools called EAP1 and EAP2. The initial magnetic bead selection strategy was continued with the EAP1 pool, and a parallel selection was carried out with the EAP2 pool where a hairpin DNA (HPD) was added to the MB-EPX suspension prior to adding the DNA pool. It is anticipated that the HPD should serve as a blocker to bind to the EPX and beads. Thus, only the high affinity and specific DNA molecules in the library should be able to bind to EPX.

After 15 rounds of selection, the DNA molecules bound to the EPX-coated beads from each selection were eluted by adding free EPX instead of heating to ensure that the DNA molecules bind to free EPX. Eluted sequences were PCR amplified and the pool was used for deep sequencing. The top 5 sequences of each selection are shown in FIG. 1C. The sequencing results revealed that most of the sequences were guanine rich, showing the presence of a G-quadruplex structure. The binding affinity of these aptamer candidates was evaluated by electrophoretic mobility shift assays (EMSA) using fluorescently labeled aptamers (FIGS. 1D and 1E). It was observed that the bands of aptamer-EPX complexes did not appear in the gel while the free aptamer band intensities diminished, leading to the finding that when the aptamer formed a complex with EPX, the fluorescence of the bound aptamer was strongly quenched. Therefore, the binding affinity of each aptamer was calculated based on the reduction of the band intensity of the free aptamer in the gels. High affinity aptamers were identified in each of the EAP1 and EAP2 pools, however, aptamer EAPi-05 was found to have the highest binding affinity with a $K_d$ of 9.2±1.6 nM (FIG. 1E). These results show that the addition of the hairpin DNA was not required to eliminate non-specifically bound DNA sequences, as both pools showed similar affinity trends.

Figure 2B:
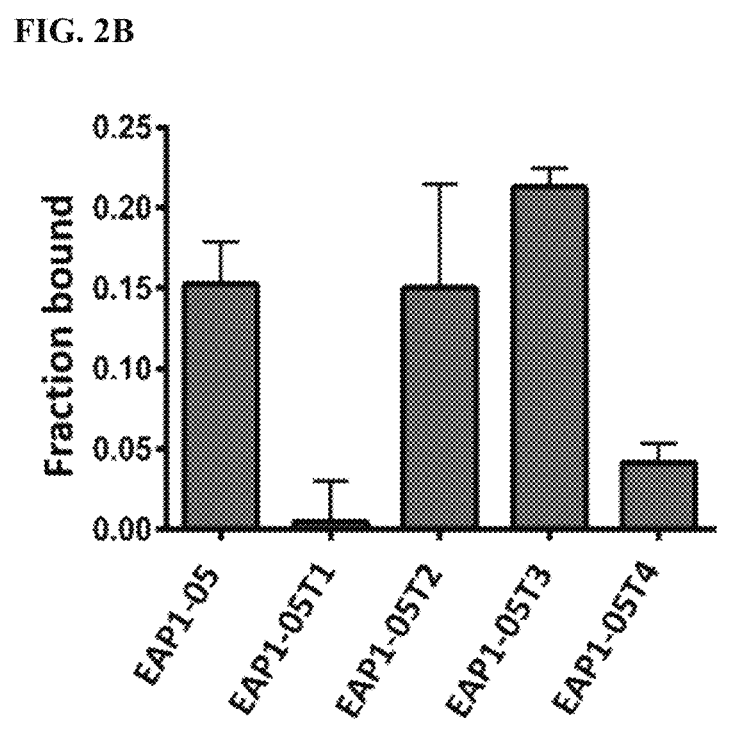
Figure 3:
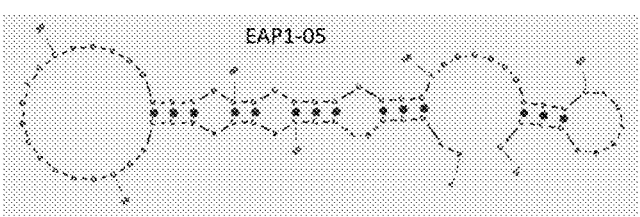
FIG. 3 shows the predicted secondary structures of EAP1-05 (SEQ ID NO: 38) and EAP1-05T3 (SEQ ID NO: 30) in exemplary embodiments of the disclosure.
Figure 3:
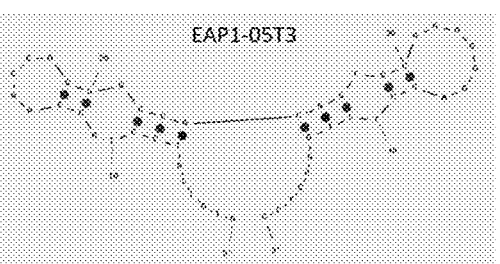

Next, EAP1-05 was subjected to truncation and deletion experiments to shorten the aptamer and improve its binding ability. The aptamer was truncated by removing various DNA segments (FIG. 2A), and the fraction of aptamer bound to EPX was assessed by EMSA using 3 nM of aptamer and a single EPX concentration of 5 nM and calculating the decrease in free aptamer fluorescence in EMSA gels. The results showed that removing the 3' stem loop of EAP1-05 significantly reduced the fraction of bound aptamer (EAP1-05T1, FIG. 2B), while deletions from the middle of the sequence had a small positive impact on EPX binding capabilities (particularly for EAP1-05T3). Switching several guanosine residues for adenosine residues also resulted in a significant reduction in EPX binding (FIG. 2, EAP1-05T4). EAP1-05T3 aptamer showed the highest degree of EPX binding, and thus was further characterized. The predicted secondary structures of EAP1-05 and EAP1-05T3 are shown in FIG. 3.

Figure 4:
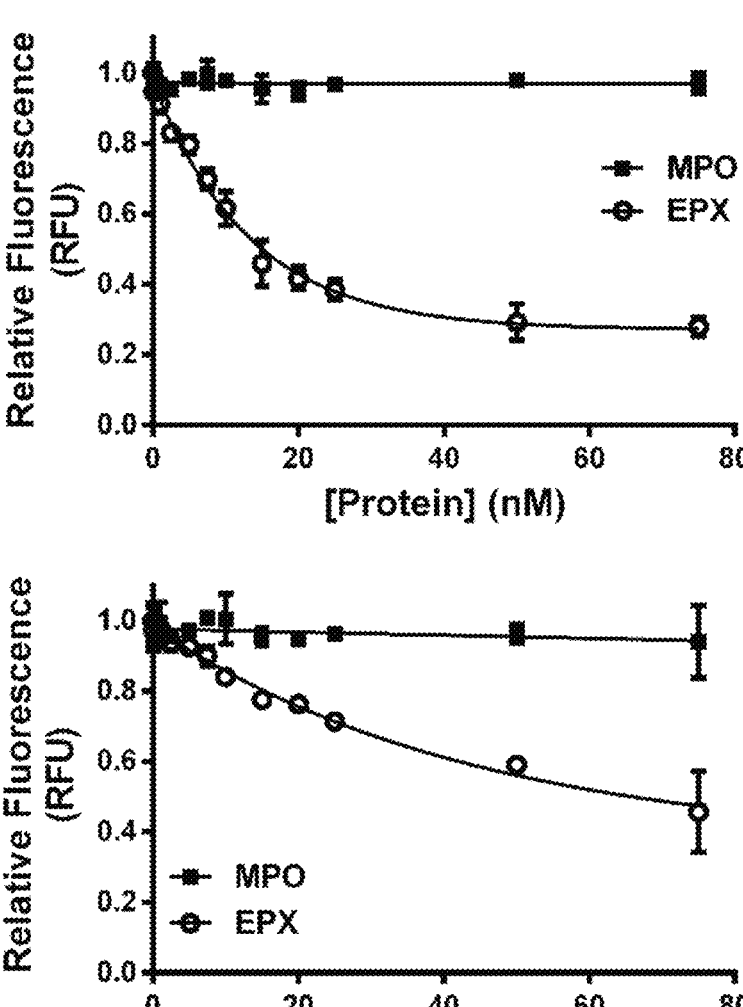
FIG. 4 shows fluorescence quenching of EPX upon binding with aptamer EAP1-05 and EAP1-05T3 in exemplary embodiments of the disclosure.
Figure 5A:
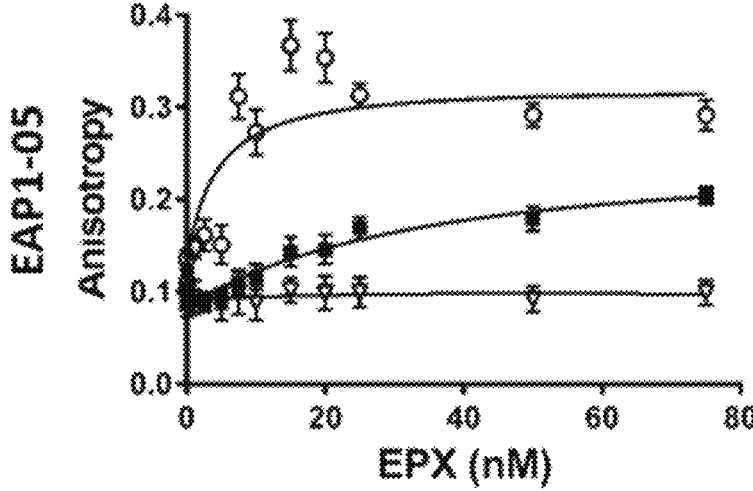
FIG. 5A shows the effect of buffer on binding affinity and specificity of the EAPi-05 and EAP1-05T3 aptamers in exemplary embodiments of the disclosure.
Figure 5B:
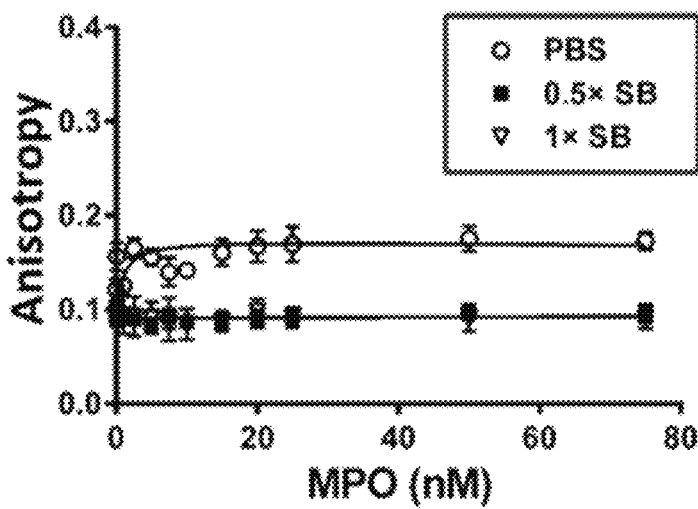
FIG. 5B shows the effect of buffer on binding affinity and specificity of the EAPi-05 and EAP1-05T3 aptamers in exemplary embodiments of the disclosure.
Figure 5C:
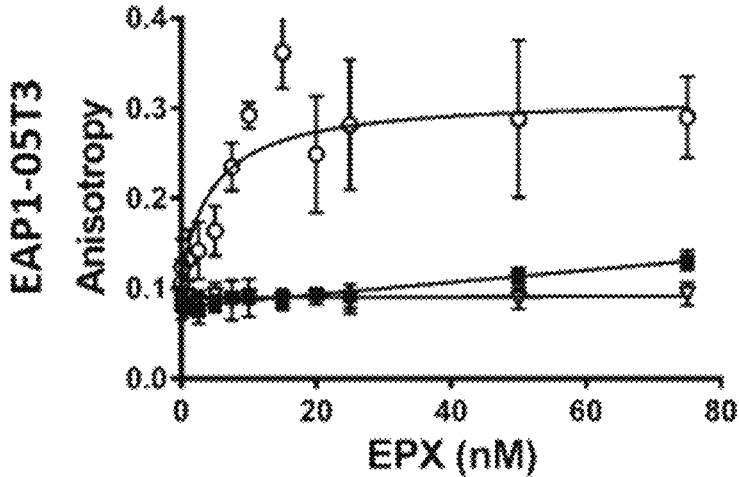
FIG. 5C shows the effect of buffer on binding affinity and specificity of the EAPi-05 and EAP1-05T3 aptamers in exemplary embodiments of the disclosure.
Figure 5D:
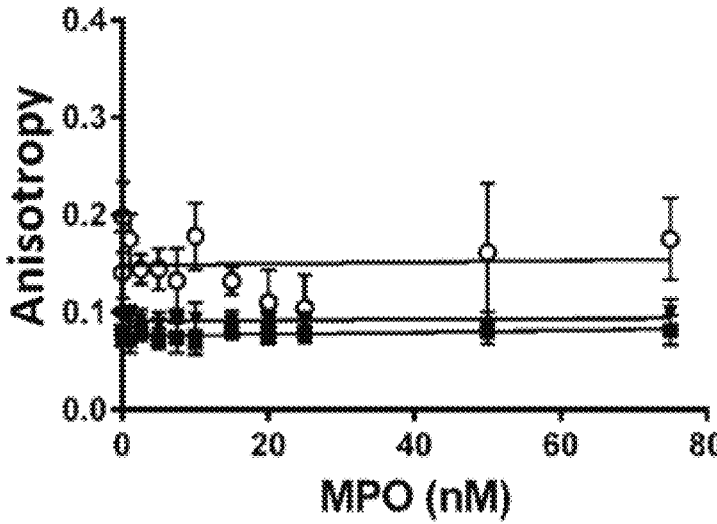
FIG. 5D shows the effect of buffer on binding affinity and specificity of the EAPi-05 and EAP1-05T3 aptamers in exemplary embodiments of the disclosure.

Initial attempts to assess the binding affinity of the aptamer using solution-based fluorescence intensity assays demonstrated that the binding of EPX lead to substantial quenching for both the native and truncated versions of the EAP1-05 aptamer (up to 70% quenching at 75 nM EPX, see FIG. 4), with minimal quenching from non-target proteins such as MPO, confirming that quenching of fluorescence was responsible for the lack of an EMSA band for the aptamer-EPX complex. Unfortunately, it was not possible to discern whether the lack of quenching from MPO was due to a lack of protein binding, or a simple lack of quenching by this protein. For this reason, fluorescence anisotropy assays were also performed with both the full length EAP1-05 and the truncated version EAP1-05T3 to assess the affinity of aptamers for EPX using different buffer conditions. No anisotropy changes were observed for either EAP1-05 or EAP1-05T3 when using the original selection buffer (1×SB; FIGS. 5A and 5C). Diluting the buffer to 0.5×SB resulted in an increase in anisotropy upon binding of EPX, with a calculated $K_d$ of 36.6±4.8 nM for the EAP1-05 aptamer (FIG. 5A). The lower salt concentration of the 0.5×SB likely results in reduced masking of charges on EPX, increasing the affinity between EPX and EAP1-05. However, it was observed that the EAP1-05T3 aptamer had very little binding affinity to EPX despite the reduced salt concentration. To further investigate the importance of the binding conditions, the interaction between EPX and EAP1-05 or EAP1-05T3 was investigated in PBS (10 mM $Na_2HPO_4$, 1.8 mM $KH_2PO_4$, 137 mM NaCl, 2.7 mM KCl, pH 7.4). The binding affinity was further improved using the lower ionic strength buffer, with a $K_d$ of 4.3±1.6 nM and 4.8±2.0 nM for EAP1-05 and EAP1-05T3, respectively (FIGS. 5A and 5C). However, the low ionic strength buffer also resulted in slightly increased non-specific binding to MPO for both aptamers (FIGS. 5B and 5D). Since both the full length and the truncated aptamer produced almost identical $K_d$ values, the truncated EAP1-05T3 aptamer was used to develop a colorimetric assay for EPX.

Figure 6A:
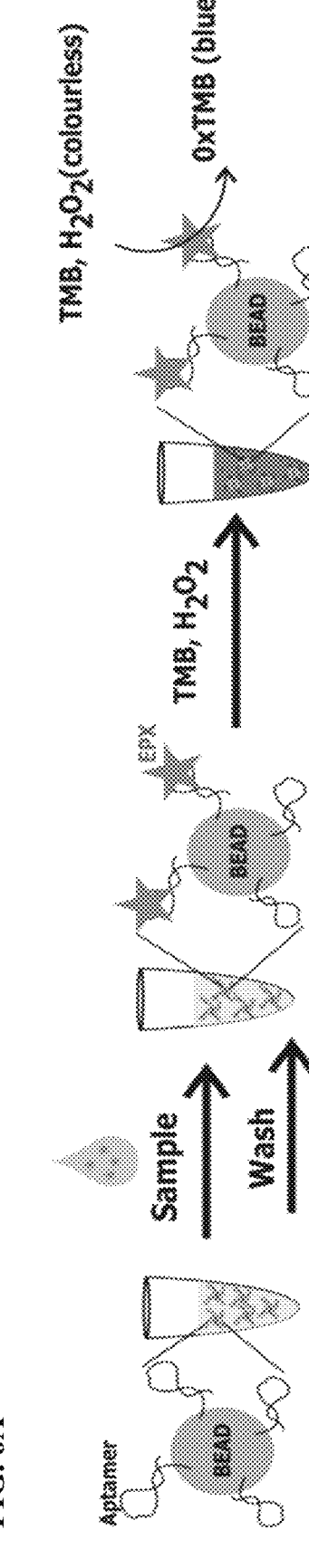
FIG. 6A shows the colorimetric assay for EPX in exemplary embodiments of the disclosure.

To generate a simple colorimetric assay for EPX, the inherent peroxidase activity of EPX to catalyze 3,3',5,5'-Tetramethylbenzidine (TMB) was utilized, which is expected to produce a blue color that can be easily seen by eye. The conceptual design of the assay is illustrated in FIG. 6A. First, a 5'-biotinylated version of EAP1-05T3 aptamer with a Tio extension was immobilized on streptavidin-coated agarose beads, washed to remove unbound aptamer sequences and suspended in the PBS binding buffer. Next, EPX was added and allowed to form a complex with the aptamer on the beads. The unbound EPX molecules in the supernatant were then removed using 3 washing cycles (300 µL PBS per washing cycle) and the beads containing the captured EPX molecules were transferred to a fresh buffer solution. Finally, a standard solution of $H_2O_2$ and TMB was added and allowed to react for 5 min to produce a blue color in the reaction tube, which was imaged with a smart phone camera. The reactions were then quenched by adding an equal volume of 0.5M HCl, producing a yellow product. This reaction mixture was transferred to a microwell plate and the absorbance was measured using a Tecan M200 plate reader operating at 450 nm.

Figure 6B:
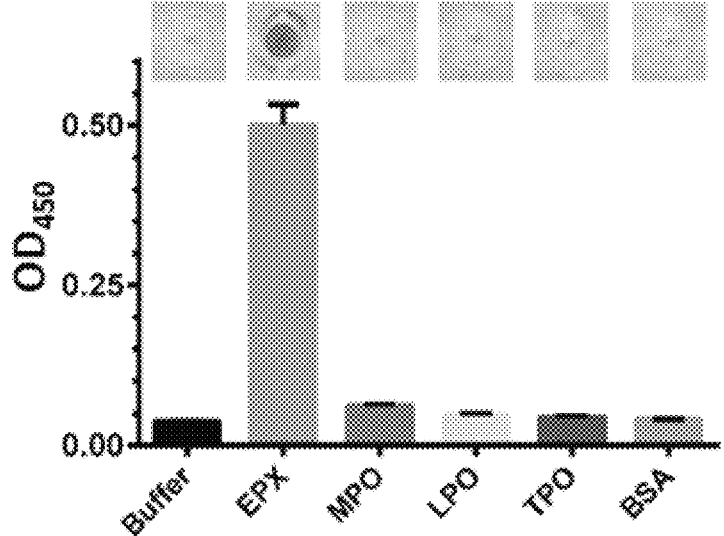
FIG. 6B shows the colorimetric assay for EPX in exemplary embodiments of the disclosure.
Figure 6C:
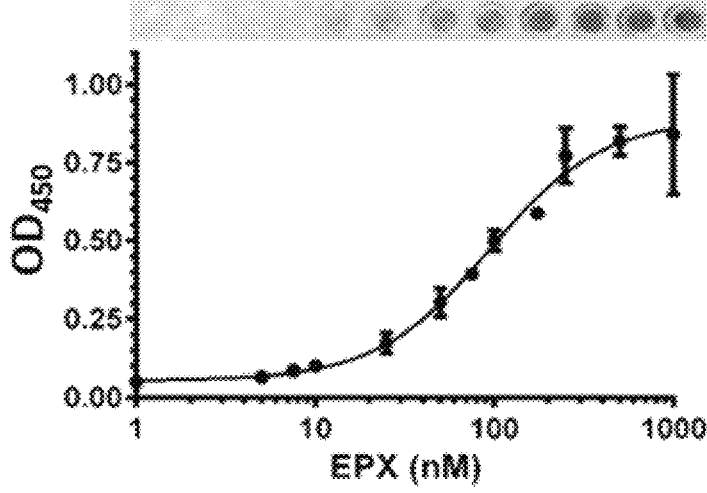
FIG. 6C shows the colorimetric assay for EPX in exemplary embodiments of the disclosure.
Figure 6D:
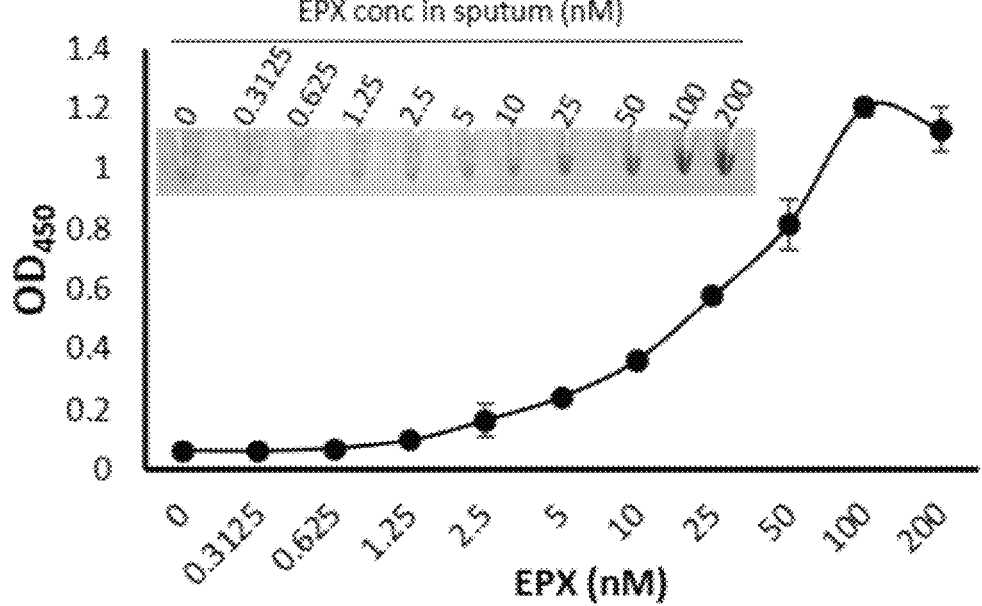
FIG. 6D shows the colorimetric assay for EPX in exemplary embodiments of the disclosure.
Figure 7:
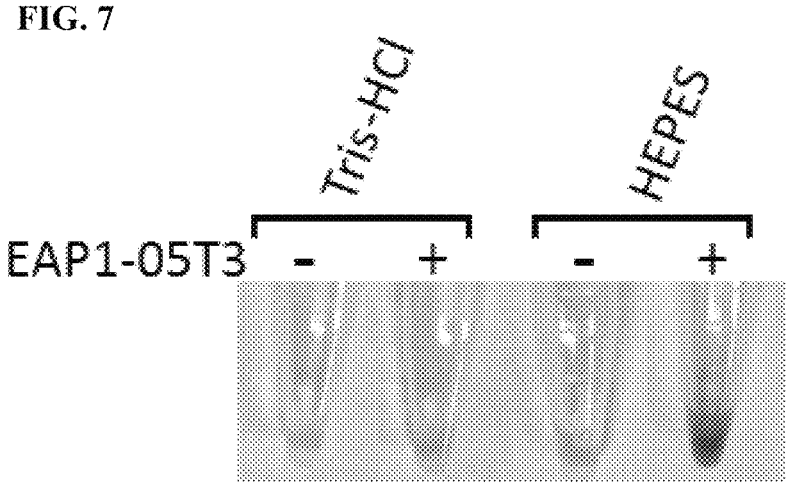
FIG. 7 shows the effect of buffer on the pulldown assay in exemplary embodiments of the disclosure.

The assay was first improved using pure EPX with two different buffer conditions: 0.5×SB and HEPES buffer (TB, see Table 2). The results presented in FIG. 7 showed that HB produced a significantly stronger color, which is consistent with the fluorescence anisotropy results that demonstrated better binding with lower ionic strength buffers. Therefore, HB was used in the TMB colorimetric assay development. Using this new buffer, the selectivity of the pull-down assay was evaluated by comparing the signal produced by EPX (100 nM) to that of several other granulocytic proteins (each at 1 µM). The results provided in FIG. 6B showed that despite the high similarity between EPX and several similar peroxidase proteins, the assay only produced a signal in the presence of EPX (FIG. 6B). This was encouraging as EPX and MPO share 70% amino acid sequence identity and 81% sequence similarity according to a protein BLAST search (EPX UniProt #P1 1678, MPO #P05164).[4] Next, the analytical sensitivity of the assay was determined using pure EPX with concentrations spanning the clinically relevant range of 1 nM-1 μM (77 ng/mL-77 μg/mL).[5,6,7] This resulted in a limit of detection (LoD) of 1 nM (blank +3σ) when using a plate reader, although the naked-eye limit of detection was approximately 25 nM (based on the images of the microwell plates shown in FIG. 6C). The LoD was also investigated in spiked sputum (20% sputum samples with varying concentrations of EPX) and produced a similar LoD of 1.25 nM using a plate reader to measure absorbance (FIG. 6D), indicating that the assay is compatible with complex sputum samples. These LOD value is also comparable to a published antibody-based EPX assay (circa 6 nM EPX).[6]

To further validate the aptamer-pulldown assay, it was next evaluated with patient sputum samples. A total of 46 sputum samples were obtained from patients (n=36) or healthy donors (n=10), with their informed consent and with approval from the Institutional Review Board (Research Ethics Board Approvals 12-3716 and 13203). Healthy donors were identified as those with no known respiratory disease, infection (or symptoms), not within 8 weeks of any vaccination, non-smoking and generally deemed to be in good health. The sputum plugs were split into two equal volumes and the first aliquot was processed using a 4:1 mixture of PBS and 0.1% dithiothreitol (DTT) as per the "gold-standard" clinical method[8] while the second aliquot was dispersed with HEPES buffer containing 2 mM DTT for use in the pull-down assay. For the gold-standard clinical method, the sputum was first centrifuged and then the suspended cells were smeared onto a slide to produce cytospin slides. The cells were then stained histologically and cellular differentials (eosinophils/neutrophils) were determined by manual counting of eosinophil and neutrophil cells, and reported as a percentage of a total of 400 cells counted by a cytologist (validated for clinical routine use[7-9]; see Table 4 for cell counts in each of the 46 samples). Matched cell-free supernatants were assessed for EPX reactivity by a traditional ELISA (Enzyme-linked immunosorbent assay) method as previously described[10,11]. Samples were designated as eosinophilic based on the presence of intact eosinophils and/or free eosinophil granules. In the event where the eosinophil numbers have been masked by high total cell count and neutrophils (in a patient undergoing an infective exacerbation), free eosinophil granules or EPX (ELISA) was used to assess the underlying eosinophilia. Based on these assays, the samples were stratified as: 1) healthy donor samples, confirmed to have no evidence of inflammation, were indicated as eosinophil (EOS) negative; 2) negative samples with <3% eosinophil content and low neutrophil counts (<64%, sputum total cell count; <9.7×10[6] cells/gm); 3) mixed samples of granulocytic sputa with total cell count <9.7×10[6] cells/gm, neutrophils >64% and eosinophils >2%, or presence of free eosinophil granules; and 4) positive samples with >3% eosinophil levels and low neutrophil counts (<64%, sputum total cell count <9.7×10[6] cells/gm). It was noted that mixed granulocytic sputa samples were considered to be EOS positive as they have evidence of eosinophil activity (free granules or EPX assay) since the the the eosinophil level is masked by high neutrophils when measured using a cell differential assay. According to the gold standard sputum cytology, 28 samples were identified as negatives and 18 were identified as mixed or positive, which is considered as 18 eosinophil positives.

Figure 8A:
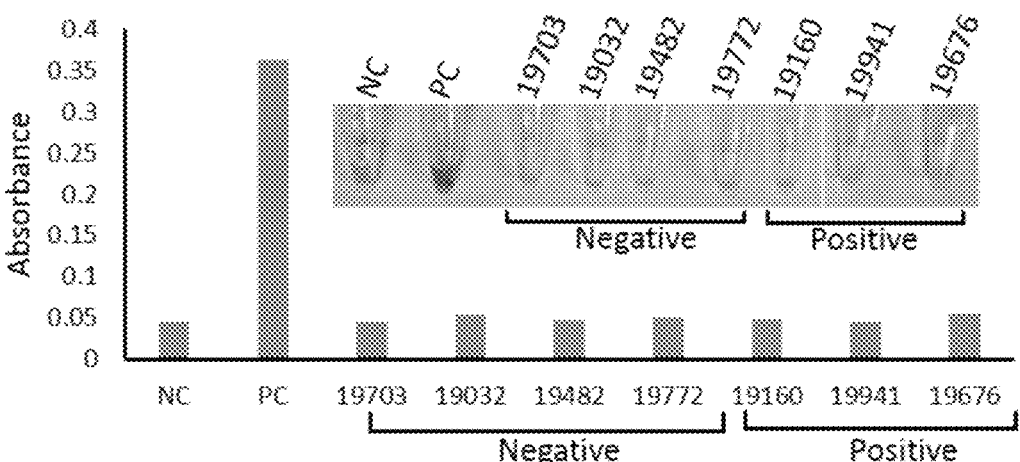
FIG. 8A shows the effect of DTT in the pulldown assay in exemplary embodiments of the disclosure.
Figure 8B:
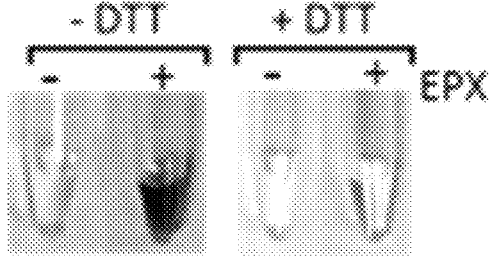
FIG. 8B shows the effect of DTT in the pulldown assay in exemplary embodiments of the disclosure.
Figure 8C:
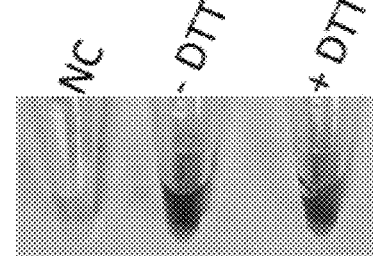
FIG. 8C shows the effect of DTT in the pulldown assay in exemplary embodiments of the disclosure.

Initial pulldown assays on patient samples used the same DTT/PBS buffer used for the gold-standard cell-counting assay. However, it was determined that this buffer was not compatible with a peroxidase assay, as an initial test of 4 negative and 3 positive samples resulted in none of the samples producing a color (FIG. 8A), even though many of the positive samples contained high amounts of EPX based on the ELISA data (FIG. 9). Further investigation of the sample processing method indicated that the high amount of DTT (0.1%) used in the routine clinical processing interfered with the EPX reaction as the hydrogen peroxide immediately reacted with the DTT (FIG. 8B). A reduction of the DTT to 2 mM in HEPES buffer (HB) produced the required dispersal of the sputum sample while retaining the ability to generate a color from the aptamer-based peroxidase assay (FIG. 8C). The final sample processing method for the pulldown assay involved dispersing the sputum samples 1:8 w/v in HEPES buffer (composition: 50 mM HEPES, 300 mM NaCl, 15 mM MgCl2, 0.01% Tween 20, 2 mM DTT). The dispersed plugs were then inverted and shaken for 5 min by hand, and then allowed to settle on ice for 2 min, after which the supernatants were aliquoted and stored at −20° C. for later analysis. Anti-protease cocktail inhibitor (Roche) containing a mixture of serine, cysteine and metalloproteases was added to each aliquot to prevent degradation of the EPX target protein. This new sputum processing method reduced both the number of steps and technical complexity of sample processing, reducing processing time from 1 h to 10 min (see FIG. 13). Since this new method of the instant disclosure simplified the sample processing using a dispersal method that requires less than 10 minutes and no specialised equipment, this method is suitable for use at the point-of-need.

FIG. 10A shows the correlation between the "gold-standard" assay and the aptamer pull-down assay. The aptamer pulldown assay was conducted on the matched "HB buffer dispersed" samples for each 46 samples and results were compared with the gold standard. The raw OD values for the assays are shown in FIG. 10A, while visual results for the assays are shown in FIG. 10B-E. Visual data for the healthy cohort samples prior to the pull-down assay are shown in FIG. 14 along with the images following the pull-down assay. This data shows that even healthy sputum samples can produce high colorimetric signals (3/10), demonstrating that simple addition of H[2]O[2]/TMB to sputum samples without the pull-down step can lead to an unacceptably high level of false positives owing to the presence of other peroxidases. Following the pull-down step, 2 of the 3 false positives show a marked reduction in color while one sample with a particularly high initial TMB signal showed a substantial reduction in color, but as seen in FIG. 10A is still observed to be a false positive. The data is plotted based on inflammatory status (gold standard): healthy (n=10; negative) and non-eosinophilic (n=18; negative); vs eosinophilic (n=12; positive) and mixed-eosinophilic (n=6; mixed). Using an OD cut-off of 0.32 based on maximizing the sum of (sensitivity+specificity) on a receiver-operator characteristic (ROC) plot (see FIG. 11), 16/18 samples are identified as true positives (sensitivity of 89%) while 27/28 samples are identified as true negatives (specificity of 96%), with an area under the curve of 88%.

Additional analysis of the assay data (FIG. 12) was performed to assess the performance of the pulldown assay for positive, mixed and negative samples, (FIG. 12A), further demonstrating that aptamer-based pulldown assay provided OD values for eosinophil samples that were significantly greater than for non-eosinophilic samples (P<0.003 in all cases), even when using mixed samples. In comparison, the OD values for eosinophilic and mixed samples had no statistical difference (P>0.999). Hence, the current pull-down assay could correctly predict eosinophilic inflammation in those samples where the routine sputum cytology using percentage of eosinophils would have failed (mixed samples). The EPX values from the pull-down assays further correlated with the percent eosinophils (FIG. 12B, r=0.59, P=0.003) and absolute eosinophils (FIG. 12C, r=0.60, P<0.001) detected in the sputum using the gold-standard clinical method, again confirming the diagnostic utility of the pulldown assay.

Given the accuracy of the aptamer-based pulldown assay for detection of EPX in clinical samples, the assay is expected to be useful in clinical practice to identify airway eosinophilia, to initiate and monitor response to anti-inflammatory treatments such as corticosteroids and anti-eosinophil biologics, and to evaluate new therapies directed against eosinophils. A key advantage of the assay is the ability to detect EPX in eosinophil positive samples even when there are high levels of anti-EPX autoantibodies present, which is not possible using antibody-based lateral flow or ELISA methods, which produce low OD values even for positive samples with high aptamer OD values (see FIG. 9). This disclosure therefore provides a simple and accurate method for quickly assessing airway eosinophilia that overcomes the drawbacks of both the current gold-standard cell differential assay and the ELISA and lateral flow assays. As such, it should be much easier to implement the pulldown assay in routine clinical practice without the need for specialized laboratory equipment or technical staff. The current method provides a clinical sensitivity of 89% and clinical specificity of 96%, which are both above the required cut-off values for routine clinical use. Moreover, this assay is suitable for high throughput analysis of patient eosinophilia without the need for measurement of cell differentials, which is a tedious and time-consuming practice.

In summary, a highly specific and sensitive DNA aptamer for EPX was obtained from a magnetic bead SELEX method. A colorimetric aptamer-pulldown assay was developed yielding a limit of detection of ~5 nM in buffer and in spiked sputum samples, which is comparable to the relevant clinical values,[5,7] and validated with clinical samples.

While the present disclosure has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

TABLES

TABLE 1

| | | DNA sequences used in this disclosure. | |
|---|---|---|---|
| SEQ ID NO | Name | Description | Sequence (5'-3') |
| 1 | DNAL | DNA Library | ATGCCATCCTACCAACN$_{40}$GAGCTCTGAACTGG |
| 2 | FP1 | Forward Primer 1 | ATGCCATCCTACCAAC |
| 3 | FP2 | Forward Primer 2 | /56-FAM/ATGCCATCCTACCAAC |
| 4 | RP1 | Reverse Primer 1 | CCAGTTCAGAGCTC |
| 5 | RP1-Anti | Reverse Primer 1 (Antisense) | GAGCTCTGAACTGG |
| 6 & 37 | RP2 | Reverse Primer 2 (SEQ ID NO: 6 and 37 linked by triethylene glycol spacer "isp9") | AAAAAAAAAAAAAAAAAAAA/isp9/CCAGTTCAGAGCTC (SEQ ID NO: 6 - AAAAAAAAAAAAAAAAAAAA) (SEQ ID NO: 37 - CCAGTTCAGAGCTC) |
| 7 | DNAB | Blocker DNA | GCGGCCCATTCTTCATTTTAGGGCCGC |
| 8 | EAP1-01 | EAP1 Aptamer Candidate 1 | ATGCCATCCTACCAAC CACGGGGATC GGGTGGGGGC TAGGCGGCGT GTGCACGGGG GAGCTCTGAACTGG |
| 9 | EAP1-05 | EAP1 Aptamer Candidate 2 | ATGCCATCCTACCAAC CAGGGGGACA GTGCAAAGGG GTAGGGAGGG GGCTAGGGGG GAGCTCTGAACTGG |
| 10 | EAP1-08 | EAP1 Aptamer Candidate 3 | ATGCCATCCTACCAAC CAGTTGCCGG TGGGGTGACC CGGTGGGGGA GGGTGTGGGG GAGCTCTGAACTGG |
| 11 | EAP1-15 | EAP1 Aptamer Candidate 4 | ATGCCATCCTACCAAC CGGGGGAGCA AGGTGTAGGG GTAGGGGGCC ATGCGAGGGG GAGCTCTGAACTGG |

TABLE 1-continued

DNA sequences used in this disclosure.

| SEQ ID NO | Name | Description | Sequence (5'-3') |
|---|---|---|---|
| 12 | EAP1-20 | EAP1 Aptamer Candidate 5 | ATGCCATCCTACCAAC AGCAGCGGGC GGGGGCCAGT GGGGGATGTA GCCGGGGGTG GAGCTCTGAACTGG |
| 13 | EAP2-01 | EAP2 Aptamer Candidate 1 | ATGCCATCCTACCAAC CGCGGGAGGA GACTGGTGTA GGGGGCATGG GATGGCCTGG GAGCTCTGAACTGG |
| 14 | EAP2-09 | EAP2 Aptamer Candidate 2 | ATGCCATCCTACCAAC ACGACCGGTG TAGAGGGGGG TATACGGAAT GGGGGTTGTG GAGCTCTGAACTGG |
| 15 | EAP2-10 | EAP2 Aptamer Candidate 3 | ATGCCATCCTACCAAC AGGGAGGGGG CGGTTAGGGA ATGGTGGTCC GGGCGGGGTA GAGCTCTGAACTGG |
| 16 | EAP2-18 | EAP2 Aptamer Candidate 4 | ATGCCATCCTACCAAC ATGGGGATAT CCGGCGGGGG CATCAGGGGG GAGTGCGGGT GAGCTCTGAACTGG |
| 17 | EAP2-40 | EAP2 Aptamer Candidate 5 | ATGCCATCCTACCAAC CAGGGGGCGC GGGAGGGGGC CTGACGTCGA GGGGGTTGGG GAGCTCTGAACTGG |
| 18 | EAP1-01-RD | EAPI Aptamer Candidate 1 RD | CACGGGGATC GGGTGGGGGC TAGGCGGCGT GTGCACGGGG |
| 19 | EAP1-05-RD | EAPI Aptamer Candidate 2 RD | CAGGGGGACA GTGCAAAGGG GTAGGGAGGG GGCTAGGGGG |
| 20 | EAP1-08-RD | EAPI Aptamer Candidate 3 RD | CAGTTGCCGG TGGGGTGACC CGGTGGGGGA GGGTGTGGGG |
| 21 | EAP1-15-RD | EAP1 Aptamer Candidate 4 RD | CGGGGGAGCA AGGTGTAGGG GTAGGGGGCC ATGCGAGGGG |
| 22 | EAP1-20-RD | EAP1 Aptamer Candidate 5 RD | AGCAGCGGGC GGGGGCCAGT GGGGGATGTA GCCGGGGGTG |
| 23 | EAP2-01-RD | EAP2 Aptamer Candidate 1 RD | CGCGGGAGGA GACTGGTGTA GGGGGCATGG GATGGCCTGG |
| 24 | EAP2-09-RD | EAP2 Aptamer Candidate 2 RD | ACGACCGGTG TAGAGGGGGG TATACGGAAT GGGGGTTGTG |
| 25 | EAP2-10-RD | EAP2 Aptamer Candidate 3 RD | AGGGAGGGGG CGGTTAGGGA ATGGTGGTCC GGGCGGGGTA |
| 26 | EAP2-18-RD | EAP2 Aptamer Candidate 4 RD | ATGGGGATAT CCGGCGGGGG CATCAGGGGG GAGTGCGGGT |
| 27 | EAP2-40-RD | EAP2 Aptamer Candidate 5 RD | CAGGGGGCGC GGGAGGGGGC CTGACGTCGA GGGGGTTGGG |
| 28 | EAP1-05T1 | Truncated EAP1-05 | CCATCCTACCAACCAGGGGGACAGTGCAAAGGGGTAG GGAG |
| 29 | EAP1-05T2 | Truncated EAP1-05 | ATGCCATCCTACCAATAGGGAGGGGGCTAGGGGGGAG CTCTGAACTCG |
| 30 | EAP1-05T3 | Truncated EAP1-05 | ATGCCATCCTACCAACCAGGGGGACAGTGCAAAGGGA GCTCTGAACTCG |
| 31 | EAP1-05T4 | Mutated EAP1-05 | ATGCCATCCTACCAACCAGAAAGACAGTGCAAAGAAA TAGAAAGAGAGCTAGAAGAAAGCTCTGAACTCG |
| 32 | EAP1-05T1FAM | Labeled Truncated EAP1-05 | /56-FAM/CCATCCTACCAACCAGGGGGACAGTGCAAAGGG GTAGGGAG |
| 33 | EAP1-05T2FAM | Labeled Truncated EAP1-05 | /56-FAM/ATGCCATCCTACCAATAGGGAGGGGGCTAGGGG GGAGCTCTGAACTCG |

TABLE 1-continued

DNA sequences used in this disclosure.

| SEQ ID NO | Name | Description | Sequence (5'-3') |
|---|---|---|---|
| 34 | EAP1-05T3FAM | Labeled Truncated EAP1-05 | /56-FAM/ATGCCATCCTACCAACCAGGGGGACAGTGCAAA GGGAGCTCTGAACTCG |
| 35 | EAP1-05T4FAM | Labeled Mutated EAP1-05 | /56-FAM/ATGCCATCCTACCAACCAGAAAGACAGTGCAAA GAAATAGAAAGAGAGCTAGAAGAAAGCTCTGAACTC G |
| 36 | EAP1-05T3BT | Biotinylated EAP1-05T3 | /5Biosg/TTTTTTTTTTATGCCATCCTACCAACCAGGGGG ACAGTGCAAAGGGAGCTCTGAACTCG |

TABLE 2

Buffers used in this disclosure.

| Name | Description | Contents |
|---|---|---|
| 1x SB | Selection buffer | 50 mM Tris, 1M NaCl, 5 mM MgCl$_2$, 2 mM KCl, 0.01 % v/v Tween 20, pH 9 |
| 1x WB | Wash buffer | 50 mM Tris, 1M NaCl, 5 mM MgCl$_2$, 2 mM KCl, 0.1 % v/v Tween 20, pH 9 |
| EB | Elution buffer | 50 mM Tris, 4M guanidine thiocyanate, 1 mM DTT, pH 9 |
| Cwb A | Coupling wash buffer A | 1 mM Ice-cold HCl |
| Cwb B | Coupling wash buffer B | 0.1M glycine, pH 2 |
| Cb | Coupling buffer | 50 mM sodium tetraborate, pH 8.5 |
| Qb | Quenching buffer | 3M ethanolamine, pH 9 |
| Sb | Storage buffer | Coupling buffer + 0.05% w/v NaN$_3$ |
| PBS | Phosphate buffer saline | 137 mM NaCl, 2.7 mM KCl. 10 mM Na$_2$HPO$_4$, 1.8 mM KH$_2$PO$_4$, pH 7.4 |
| HB | HEPES buffer | 50 mM HEPES, 300 mM NaCl, 15 mM MgCl$_2$, 0.01% Tween20, pH 7.5 |

TABLE 3

SELEX outline for the EAPTI and EAPT2 selections including times and values used; T1 selection was performed without the blocker oligo, while the T2 selection was performed with the blocker oligo.

| Round | DNA library (pmol) | Beads | Positive selection time (minutes) | Negative selection (minutes) | Blocker DNA, pmol (blocker: target) |
|---|---|---|---|---|---|
| 1 | 1000 | 1 × 10$^7$ beads | 120 | 30 | 500 (10:1) |
| 2 | ~50 | 1 × 10$^6$ beads | 60 | | 50 (10:1) |
| 3 | | 1 × 10$^6$ beads | 60 | 30 | 50 (10:1) |
| 4 | | 1 × 10$^6$ beads | 30 | | 100 (20:1) |
| 5 | | 1 × 10$^5$ beads | 30 | 30 | 10 (20:1) |
| 6 | | 1 × 10$^5$ beads | 15 | | 10 (20:1) |
| 7 | | 1 × 10$^5$ beads | 15 | 30 | 20 (40:1) |
| 8 | | 1 × 10$^4$ beads | 15 | | 2 (40:1) |
| 9 | | 1 × 10$^4$ beads | 15 | 30 | 2 (40:1) |
| 10 | | 1 × 10$^4$ beads | 10 | | 2 (40:1) |
| 11 | | 1 × 10$^4$ beads | 10 | 30 | 4 (80:1) |
| 12 | | 1 × 10$^4$ beads | 10 | | 4 (80:1) |
| 13 | | 1 × 10$^4$ beads | 5 | 30 | 8 (160:1) |
| 14 | | 1 × 10$^4$ beads | 5 | | 8 (160:1) |
| 15 | | 1 × 10$^4$ beads | 5 | 30 | 8 (160:1) |

TABLE 4

Airway inflammatory status for individual patients based on sputum cytology.

| Patient Number | Intact Sputum Eosinophils (%) | Free Eosinophil Granules (FEGs) | Inflammatory phenotype | Inflammatory status (Eos. = 1, Non-eos. = 0) | OD from aptamer pull-down assay (cut-off, 0.32) | Agreement with gold standard (yes = 1) |
|---|---|---|---|---|---|---|
| Healthy Controls | | | | | | |
| H1 | 0 | 0 | Pauci | 0 | 0.1202 | 1 |
| H2 | 0 | 0 | Pauci | 0 | 0.0969 | 1 |
| H3 | 0 | 0 | Pauci | 0 | 0.1393 | 1 |
| H4 | 0 | 0 | Pauci | 0 | 0.1605 | 1 |
| H5 | 0 | 0 | Pauci | 0 | 0.0989 | 1 |
| H6 | 0.5 | 0 | Pauci | 0 | 0.0930 | 1 |
| H7 | 0 | 0 | Pauci | 0 | 0.2974 | 1 |
| H8 | 0.3 | 0 | Pauci | 0 | 0.0936 | 1 |
| H9 | 1.3 | 0 | Pauci | 0 | 0.4603 | 0 |
| H10 | 0 | 0 | Pauci | 0 | 0.1432 | 1 |
| Clinically-indicated Patients | | | | | | |
| P1 | 0 | 0 | Trivial | 0 | 0.1436 | 1 |
| P2 | 0 | 0 | Neutrophilic Pauci | 0 | 0.2085 | 1 |
| P3 | 0.7 | 0 | Pauci | 0 | 0.2402 | 1 |
| P4 | 0 | 0 | Infective | 0 | 0.2281 | 1 |
| P5 | 0 | 0 | Neutrophilic Pauci | 0 | 0.0968 | 1 |
| P6 | 0.5 | 0 | Infective | 0 | 0.1114 | 1 |
| P7 | 0.3 | 0 | Neutrophilic Pauci | 0 | 0.1829 | 1 |
| P8 | DG* | 0 | Pauci | 0 | 0.0939 | 1 |
| P9 | 0.5 | 0 | Infective | 0 | 0.0976 | 1 |
| P10 | 0 | 0 | Neutrophilic Pauci | 0 | 0.1042 | 1 |
| P11 | 0.8 | 1 | Pauci | 1 | 0.1088 | 0 |
| P12 | 0.3 | 0 | Pauci | 0 | 0.3127 | 1 |
| P13 | 0 | 0 | Pauci | 0 | 0.1090 | 1 |
| P14 | 0 | 0 | Infective | 0 | 0.2298 | 1 |
| P15 | 0 | 0 | Neutrophilic Pauci | 0 | 0.1790 | 1 |
| P16 | 0.3 | 0 | Infective | 0 | 0.2109 | 1 |
| P17 | 0.8 | 1 | Neutrophilic Pauci | 1 | 0.1030 | 1 |
| P18 | 0 | 0 | Infective | 0 | 0.1558 | 1 |
| P19 | 0 | 0 | Neutrophilic Infective | 0 | 1.4479 | 0 |
| P20 | 39.8 | 3 | Neutrophilic Eosinophilic | 1 | 1.0566 | 1 |
| P21 | 0.5 | 0 | Infective | 0 | 0.8023 | 0 |
| P22 | 0.3 | 0 | Neutrophilic Infective | 0 | 0.3890 | 0 |

TABLE 4-continued

Airway inflammatory status for
individual patients based on sputum cytology.

| Patient Number | Intact Sputum Eosino-phils (%) | Free Eo-sino-phil Gran-ules (FEGs) | Inflam-matory pheno-type | Inflam-matory status (Eos. = 1, Non-eos. = 0) | OD from aptamer pull-down assay (cut-off, 0.32) | Agree-ment with gold stan-dard (yes = 1) |
|---|---|---|---|---|---|---|
| P23 | DG* | 3 | Eosinophilic | 1 | 1.0331 | 1 |
| P24 | 17.8 | 1 | Mixed | 1 | 0.6264 | 1 |
| P25 | 1 | 1 | Mixed | 1 | 0.8018 | 1 |
| P26 | 12.1 | 3 | Eosinophilic | 1 | 0.4084 | 1 |
| P27 | 8 | 3 | Eosinophilic | 1 | 0.3573 | 1 |
| P28 | DG* | 3 | Eosinophilic | 1 | 0.7481 | 1 |
| P29 | 13.3 | 3 | Mixed | 1 | 1.1791 | 1 |
| P30 | 37.5 | 3 | Eosinophilic | 1 | 1.1612 | 1 |
| P31 | DG* | 3 | Eosinophilic | 1 | 1.0408 | 1 |
| P32 | DG* | 1 | Pauci | 1 | 0.2639 | 1 |
| P33 | 3.5 | 0 | Eosinophilic | 1 | 0.7202 | 1 |
| P34 | 8.5 | 3 | Eosinophilic | 1 | 1.2495 | 1 |
| P35 | 70 | 3 | Eosinophilic | 1 | 0.4366 | 1 |
| P36 | 4.3 | 1 | Eosinophilic | 1 | 0.1157 | 0 |

REFERENCES (1) Bruno, J. G. *Biochem. Biophys. Res. Commun* 1997, 234 (1), 117-120.

(2) Duan, N.; Wu, S.; Chen, X.; Huang, Y.; Xia, Y.; Ma, X.; Wang, Z. *J. Agric. Food Chem* 2013, 61, 3229-3234.

(3) Ali, M. M.; Aguirre, S. D.; Lazim, H.; Li, Y. *Angew. Chemie Int. Ed.* 2011, 50 (16), 3751-3754.

(4) Altschul, S. F.; Madden, T. L.; Schaffer, A. A.; Zhang, J.; Zhang, Z.; Miller, W.; Lipman, D. J. 1997, 25 (17), 3389-3402.

(5) Ochkur, S. I.; Kim, J. D.; Protheroe, C. A.; Colbert, D.; Condjella, R. M.; Bersoux, S.; Helmers, R. A.; Moqbel, R.; Lacy, P.; Kelly, E. A.; Jarjour, N. N.; Kern, R.; Peters, A.; Schleimer, R. P.; Furuta, G. T.; Nair, P.; Lee, J. J.; Lee, N. A. *J. Immunol. Methods* 2012, 384 (1-2), 10-20.

(6) Wolfe, M. G.; Mukherjee, M.; Radford, K.; Brennan, J. D.; Nair, P. *Allergy* 2018, 74(1), 1-3.

(7) Nair, P.; Ochkur, S. I.; Protheroe, C.; Radford, K.; Efthimiadis, A.; Lee, N. A.; Lee, J. *J. Allergy Eur. J. Allergy Clin. Immunol.* 2013, 68 (9), 1177-1184.

(8) You M, Peng P, Xue Z, Tong H, He W, Mao P, Liu Q, Yao C, Xu F. A fast and ultrasensitive ELISA based on rolling circle amplification. *Analyst* 2021 146 (9), 2871-2877.

(9) Pizzichini E, Pizzichini M M M, Efthimiadis A, Hargreave F E, Dolovich J. Measurements of inflammatory indices in induced sputum: effects of selection of sputum to minimize salivary contamination. *Eur Respir J* 1996 9.

(10) Kjarsgaard M, Adatia A, Bhalla A, LaVigne N, Radford K, Huang C, Mukherjee M, Nair P. Underestimation of airway luminal eosinophilia by quantitative sputum cytometry. Allergy Asthma Clin Immunol 2021 17: 63.

(11) Belda J, Leigh R, Parameswaran K, O'Byrne P M, Sears M R, Hargreave F E. Induced sputum cell counts in healthy adults. *Am J Respir Crit Care Med* 2000 161, 475-478.

(12) Sajid M, Kawde A and Daud M. Design, Formats and Applications of Lateral Flow Assays, *J Saudi Chem Soc.,* 2015 19, 689-705.

(13) Bahadir E B & Sezgintürk MK. Lateral flow assays: Principles, designs and labels. *Trends in Analytical Chemistry,* 2016 82, 286-306.

The invention claimed is:

1. A DNA aptamer that binds eosinophil peroxidase, wherein the aptamer comprises the sequence of SEQ ID NO: 30, 9, or 36.

2. A DNA aptamer that binds eosinophil peroxidase, wherein the aptamer consists of the sequence of SEQ ID NO: 30, 9, or 36.

3. The aptamer of claim 1, further comprising an immobilization linker.

4. The aptamer of claim 3, wherein the immobilization linker is biotin.

5. An aptamer probe comprising the aptamer of claim 1 and a detectable label.

6. The aptamer probe of claim 5, wherein the detectable label comprises a fluorescent, a colorimetric or other optical probe or electrochemical moiety.

7. A method for detecting the presence of eosinophil peroxidase in a sample, the method comprising:
   a) contacting the sample with the aptamer probe of claim 5, and
   b) detecting a signal generated from binding of the aptamer with the eosinophil peroxidase, wherein detecting the signal indicates the presence of the eosinophil peroxidase in the sample.

8. The method of claim 7, further comprising dispersing the sample in a buffer solution comprising about 2 mM dithiothreitol before step a), optionally the buffer solution comprises HEPES.

9. The method of claim 8, wherein the sample is a sputum sample.

10. A method for detecting the presence of eosinophil peroxidase in a sample, the method comprising:
   a) contacting the sample with an immobilized aptamer of claim 1 in a first buffer solution;
   b) allowing the immobilized aptamer to bind to the eosinophil peroxidase to form an immobilized aptamer-eosinophil peroxidase complex;
   c) transferring the immobilized aptamer-eosinophil peroxidase complex to a second buffer solution;
   d) adding a solution of $H_2O_2$ and 3,3',5,5'-tetramethylbenzidine to the second buffer solution; and
   e) detecting a colorimetric signal;
   wherein detecting the colorimetric signal indicates the presence of eosinophil peroxidase in the sample.

11. The method of claim 10, further comprising, before step c), washing the immobilized aptamer-eosinophil peroxidase complex with a washing buffer, optionally washing up to 3 times before step c).

12. The method of claim 10, further comprising dispersing the sample in a buffer solution comprising about 2 mM dithiothreitol before step a), optionally the buffer solution comprises HEPES.

13. The method of claim 10, wherein the sample is a sputum sample.

14. A kit for detecting eosinophil peroxidase, wherein the kit comprises the aptamer of claim 1 and instructions for use of the kit.

15. The kit of claim 14, further comprising a solution comprising $H_2O_2$ and 3,3',5,5'-tetramethylbenzidine.

16. The kit of claim 14, further comprising a buffer solution for dispersing a sample, wherein the buffer solution comprises 2 mM dithiothreitol, optionally the buffer solution comprises HEPES.

17. The kit of claim 14, wherein the kit further comprises one or more buffers.

* * * * *